United States Patent [19]

Bianconi

[11] Patent Number: 5,516,884
[45] Date of Patent: May 14, 1996

[54] PREPARATION OF POLYCARBYNES AND DIAMOND-LIKE CARBON MATERIALS MADE THEREFROM

[75] Inventor: Patricia A. Bianconi, State College, Pa.

[73] Assignee: The Penn State Research Foundation, University Park, Pa.

[21] Appl. No.: 208,262

[22] Filed: Mar. 9, 1994

[51] Int. Cl.$^6$ ............................ C07C 13/28; C08G 61/00
[52] U.S. Cl. ............................ 528/397; 585/17; 585/19; 585/20; 585/23; 585/352
[58] Field of Search ............................ 585/17, 22, 352, 585/19, 20, 23; 528/394, 397, 401

[56] References Cited

U.S. PATENT DOCUMENTS

| 5,053,434 | 10/1991 | Chapman | 585/352 |
| 5,306,851 | 4/1994 | Wu et al. | 585/22 |
| 5,345,020 | 9/1994 | Shen et al. | 585/352 |

OTHER PUBLICATIONS

"Poly(phenylcarbyne): A Polymer Precursor to Diamond–like Carbon" Visscher et al., Science Jun. 1993.
Bianconi et al., Macromolecules, V22 Dec. 1989.
Poly(phenylcarbyne): A Polymer Precursor to Diamond–Like Carbon, Glenn T. Visscher, David C. Nesting, John V. Badding, Patricia A. Bianconi, Science, vol. 260, Jun. 4, 1993, pp. 1496–1499.
Abstract for "Synthesis and Characterization of Polycarbynes, a New Class of Carbon–Based Network Polymers", Glenn T. Visscher and Patricia A. Bianconi, Advance ACS Abstracts, Jan. 1, 1994.
Bianconi, P. A.; Weidman, T. W., Journal of the American Chemical Society, vol. 110, p. 2342, Dec. 1988.
Bianconi, P. A.; Schilling, F. C.; Weidman, T. W. Macromolecules, vol. 22, p. 1967, Dec. 1989.
Eaton, P. E., Angew. Chem. Int. Ed. Engl., vol. 31, p. 1421, Dec. 1992.
"Polysilyne–co–Polytityne Network Polymers as SiC and TiC Precursors", M. S. Knapp, T. A. Manninen, P. A. Bianconi, and G. L. Messing, Abstracts of Papers, 1993 Spring Meeting of the Materials Research Society, San Francisco, CA; Materials Research Society: Pittsburgh, PA H1.12,I2.12. Dec. 1993.
Eaton, P. E., Angew. Chem. Int. Ed. Engl. vol. 31, p. 1421–1436.
CA: 111:102,908, Dec. 1989.

Primary Examiner—Morton Foelak
Assistant Examiner—John M. Cooney, Jr.
Attorney, Agent, or Firm—Thomas J. Monahan

[57] ABSTRACT

Synthesis and characterization of polycarbynes, a new class of carbon-based random network polymers. The network backbones of the polymers are composed of tetrahedrally hybridized carbon atoms, each bearing one substituent and linked via three carbon-carbon single bonds into a three-dimensional continuous random network backbone. Silicon, germanium, tin, lead, Group 13 through Group 16 elements, lanthanides, and Group 4 metals can be incorporated into the polymer backbone. The atomic-level carbon network backbone confers unusual properties on the polymers, including thermal decomposition to form diamond or diamond-like carbon.

5 Claims, 7 Drawing Sheets

PREPARATION OF POLYCARBYNES AND DIAMOND-LIKE CARBON MATERIALS MADE THEREFROM

Part of the work performed during development of this invention utilized U.S. Government funds, supported under the National Science Foundation, Division of Materials Research grant DMR-8919049. The U.S. Government has certain rights in this invention.

FIELD OF THE INVENTION

The present invention relates to a new class of carbon-based network polymers, known as polycarbynes, and methods of synthesis and utilization of same to form diamond or diamond-like carbon phases by various processes.

BACKGROUND OF THE INVENTION

The polyacetylene class of polymers of stoichiometry $[CR]_n$ have long been a focus of intense research due to their conductive and electronic properties (T. A. Skotheim, Handbook of Conducting Polymers, Marcel Dekker: New York, ed. 1986, vol 1 and 2; J. C. W. Chien, Polyacetylenes: Chemistry, Physics, and Material Science; Academic Press, Orlando, 1984). These polymers have linear backbones consisting of alternating C—C and C=C bonds, each C bearing one substituent. Recently inorganic backbone polymers of similar stoichiometry, but different structure, have been synthesized: the polysilynes $[SiR]_n$ and the polygermynes $[GeR]_n$ and their copolymers (P. A. Bianconi, T. W. Weidman, *J. Am. Chem. Soc.* 110, 2342, 1988; P. A. Bianconi, F. C. Schilling, T. W. Weidman, *Macromolecules* 22, 1697, 1989; T. W. Weidman, P. A. Bianconi, E. W. Kwock, *Ultrasonics* 28, 310, 1990; K. Furukawa, M. Fujino, M. Matsumoto, *Macromolecules* 23, 3423, 1990; P. A. Bianconi, T. W. Weidman, E. W. Kwock, in Polymers For Lightwave and Integrated Optics: Technology and Applications, L. Hornak, Optical Engineering Series, ed. Marcell Decker: New York, 1991, pp. 195–207). These polymers have a continuous random network backbone, each inorganic atom being tetrahedrally hybridized and bound via single bonds to three other inorganic atoms and one substituent. The network polymers show novel properties compared to linear inorganic backbone polymers due to the characteristics conferred by the network structure. A carbon-based continuous random network backbone polymer of $[CR]_n$ stoichiometry has never been reported, although oligomers of this structure, the cubanes ($C_8R_8$) and dodecahedranes ($C_{20}R_{20}$), are known (P. E. Eaton, *Angew. Chem. Int. Ed. Engl.* 31:1421 (1992); G. A. Olah, G. K. Surya Prakash, T. Kobayashi, L. A. Paquette, *J. Am. Chem. Soc.* 110, 1304, 1988).

That the linear structure is preferred over a random network structure of single bonds in $[CR]_n$ carbon polymers is to be expected, given the much greater strength of C=C over Si=Si or Ge=Ge bonds (Gusel'nikov, L. E.; Nametkin, N. S. Chem. Rev 1979, 79, 529). Therefore the possibilities of synthesis of the carbon-based network polymer of $[CR]_n$ stoichiometry was often questioned by the expert in the field.

Contrary to the belief that such materials cannot exist as stable compounds, the present invention describes the first evidence of the synthesis and properties of polycarbynes $[CR]_n$, the network backbone which is composed of $sp^3$-hybridized carbon atoms which bear one substituent and are linked through three single C—C bonds into a continuous random network of fused rings. Polycarbyne polymers may also include unsubstituted carbons which are connected by four single C—C bonds to the network, these atoms thus having no R substituent. Polycarbynes constitute a new class of carbon-based network polymers. The continuous random network carbon backbone confers unique properties on these polymers including facile conversion to diamond or diamond-like carbon. Applicants present herein full synthetic and characterization procedures for polycarbynes, as well as the syntheses of network copolymers of carbynes and inorganic-based monomers.

SUMMARY OF THE INVENTION

In accordance with the present invention, a new class of carbon-based random network polymers, referred to as polycarbynes, and methods related to synthesis and utilization thereof are presented. The polymers, which can be characterized as compounds composed of tetrahedrally-hybridized carbon atoms, each bearing one substituent and linked via three carbon-carbon single bonds into a three dimensional continuous random network of fused rings have unusual properties including facile thermal decomposition to form diamond or diamond-like carbon phases. The polycarbyne polymers of the present invention also include polymers having carbon or other network backbone atoms connected to the network backbone by four single bonds, these atoms thus having no R substitutent. Silicon, germanium, tin, lead, Group 13 through Group 16 elements, Lanthanides, and Group 4 metals can be incorporated into the polymer backbone. Methods of synthesis of silyne/carbyne network copolymers are also presented as well as methods of incorporation of other metals and elements into the polymers to form precursors for manufacturing materials of unusual properties.

OBJECTS OF THE INVENTION

An object of this invention is to provide novel carbon-based random network polymers and silyne/carbyne network copolymers, as well as such polymers and copolymers with other metals and elements incorporated within, which have unusual properties including facile thermal decomposition to form diamond or diamond-like carbon phases.

Another object of this invention is to provide methods of synthesis of the said polymers and silyne/carbyne network copolymers, as well as methods of incorporation of other metals and elements into the polymers.

It is also an object of this invention to provide a method for using the said polymers and copolymers to produce diamond or diamond-like materials. These and other objects and advantages of the invention over the prior art and a better understanding of its use will become readily apparent from the following description and art particularly delineated in the appended claims.

BRIEF DESCRIPTION OF THE DRAWINGS

The invention will be better understood with respect to the accompanying drawings, in which.

DESCRIPTION OF THE PREFERRED EMBODIMENTS

Figure 1:
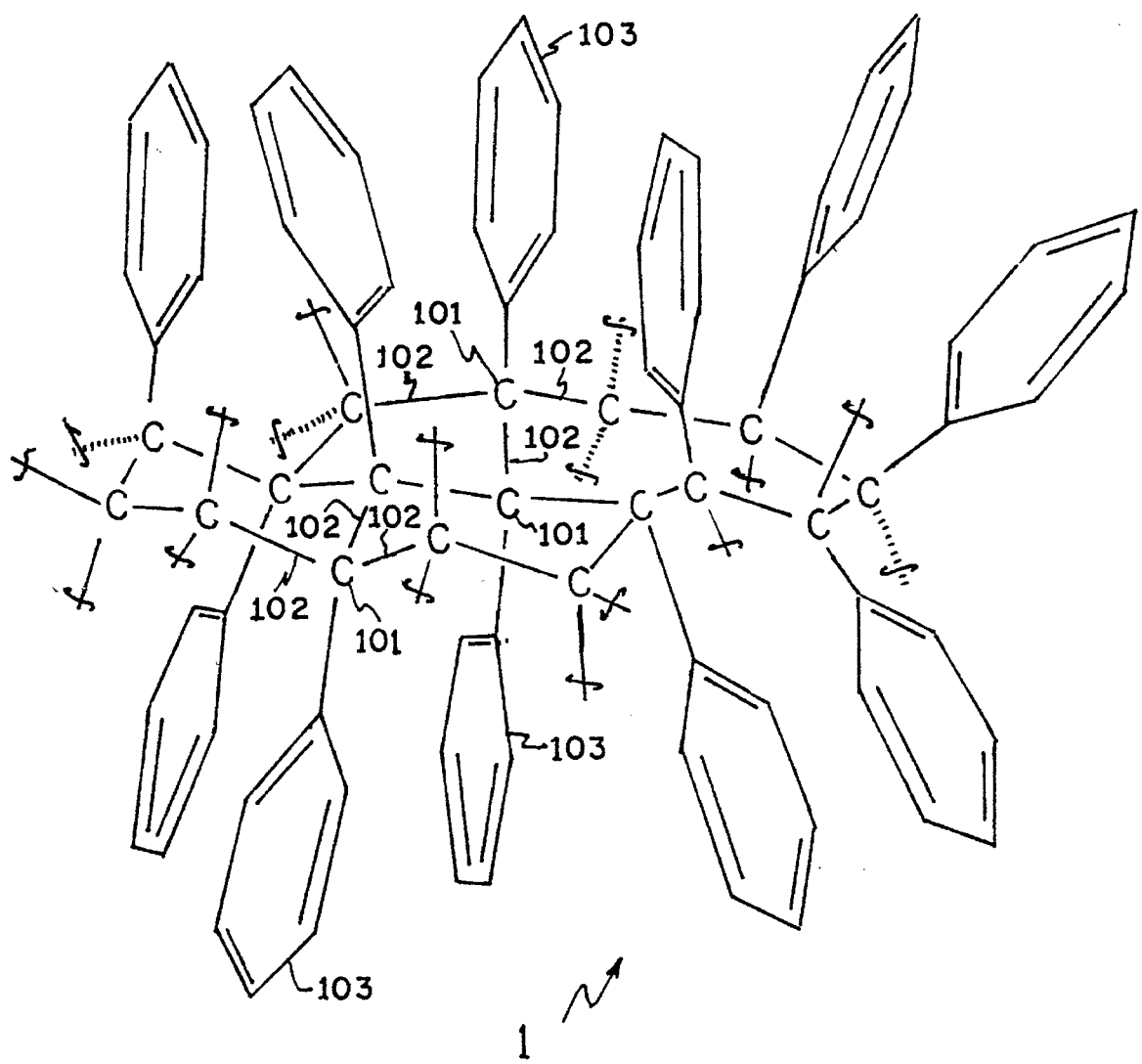
FIG. 1 shows a schematic representation of the proposed network structure of poly(phenylcarbyne) 1.

I. Characterization and Structure of the Polymers

The polymers of the present invention include those of the polycarbyne class, having the general formula $[CR]_n$. Substituent R can be hydrogen (H) or a saturated linear or branched-chain hydrocarbon containing from 1 to 30 carbon atoms, an unsaturated ring hydrocarbon containing 5 to 14 carbon atoms in the ring, each in unsubstituted or substituted form, wherein substituent groups include at least one of halogen, nitro, cyano, alkoxy, carboxy, aryl, hydroxy, heterocyclic alkyl, or heterocyclic aryl groups, a halogen, a Group 4 metal, or a Group 13 through Group 16 element. Silyne polymers (described more fully in Section II below) have been made with R being an 18-carbon chain group and with R being a polymer chain group (where a polymer is defined as having more than 20 repeat units). The degree of polymerization can be up to several hundred. R can also be a halogen (typically fluorine, chlorine, bromine, iodine), any Group 13 through Group 16 element (typically boron, aluminum, gallium, indium, thallium, carbon, silicon, germanium, tin, lead, nitrogen, phosphorous, arsenic, antimony, bismuth, oxygen, sulfur, selenium, tellurium) or compounds of any Group 13 through Group 16 element, any Group 4 metal (typically titanium, zirconium, hafnium), or compounds of any Group 4 metal, any Lathananide, or any transition metal (Group 3 through Group 12). R can also be an organic group or polymer containing heteroatoms such as nitrogen (N), oxygen (O), sulfur (S), halogens, any Group 13 through Group 16 element, any Group 4 metal, any Lanthanide, or any transition (Group 3 through Group 12) metal. Typical Group 3 through Group 12 metals include Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. Silyne polymers have been made with heteroatoms with nitrogen, oxygen, and halogens.

The degree of polymerization of the polycarbynes is defined by "n". While the upper limit of n may be greater, carbyne polymers have been made where n was approximately equal to 1,200. The lower limit of n is approximately equal to 8. Silyne polymers have been made where n is approximately equal to 8.

The polymers of the present invention are structurally configured of tetrahedrally hybridized carbon atoms linked by three carbon-carbon single bonds into a three-dimensional continuous random network backbone, each carbon atom bearing one substituent. The phrase "tetrahedrally hybridized" is understood to mean that each carbon atom in the polymer backbone bonds to four other atoms, either backbone or substituent atoms, which are dispersed around the carbon atom in an (approximately) tetrahedral geometry. This is also known as "sp$^3$-hybridized" carbon, meaning that the bonds to the four other atoms are formed using the carbon's four sp$^3$ atomic orbitals. However, many of the polycarbynes may contain a small amount of "trigonally-hybridized" or "sp$^2$-hybridized" carbon, in other words carbon-carbon double bonds, as impurities. The backbone itself is composed primarily of the tetrahedrally-hybridized carbon. A first group of polymers have pure R substituents, and a second group a co-mixture of different substituents. A third group of polymers of the present invention include silyne/carbyne network copolymers resulting from incorporation of Si into the network backbone, as well as copolymers which incorporate other element or metal atoms into the network backbone. The Si or other inorganic and metal atoms adopt bonding geometries depending upon their own requirements.

A fourth group of polymers of the present invention include polymers having carbon or other network backbone atoms connected to the network backbone by four single bonds, these atoms thus having no R substituent. Such network backbone atoms which can be incorporated without any R substituent include carbon, silicon, germanium, titanium, other metal atoms, or other Group 13 through Group 16 elements. Thus, the polymers of the present invention can be characterized as carbyne/tetrahedral carbon network backbone copolymers, or carbyne/inorganic element network copolymers.

Because of the belief that polymers of the structure reported herein could not exist as it would not be expected that carbon would act like an inorganic element, extensive testing, modeling, and analysis were performed to confirm the polycarbyne structure. A discussion of these results follows.

The synthesis of $[CR]_n$ and various copolymers is detailed in Section II below. For R=phenyl, poly(phenylcarbyne) (1) is obtained in accordance with Equation 1 as a tan powder which is soluble in common organic solvents.

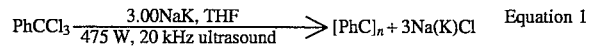

$$PhCCl_3 \xrightarrow[475 \text{ W, } 20 \text{ kHz ultrasound}]{3.00 \text{NaK, THF}} [PhC]_n + 3Na(K)Cl \qquad \text{Equation 1}$$

Insoluble crosslinked material and low molecular weight oligomers are the only other products. Chemical analysis of 1 was consistent with the empirical formula $[C_6H_5C]_n$, and gel permeation chromatography (GPC) of the material gave $M_W$=4000, indicating that 1 is polymeric.

Figure 5A:
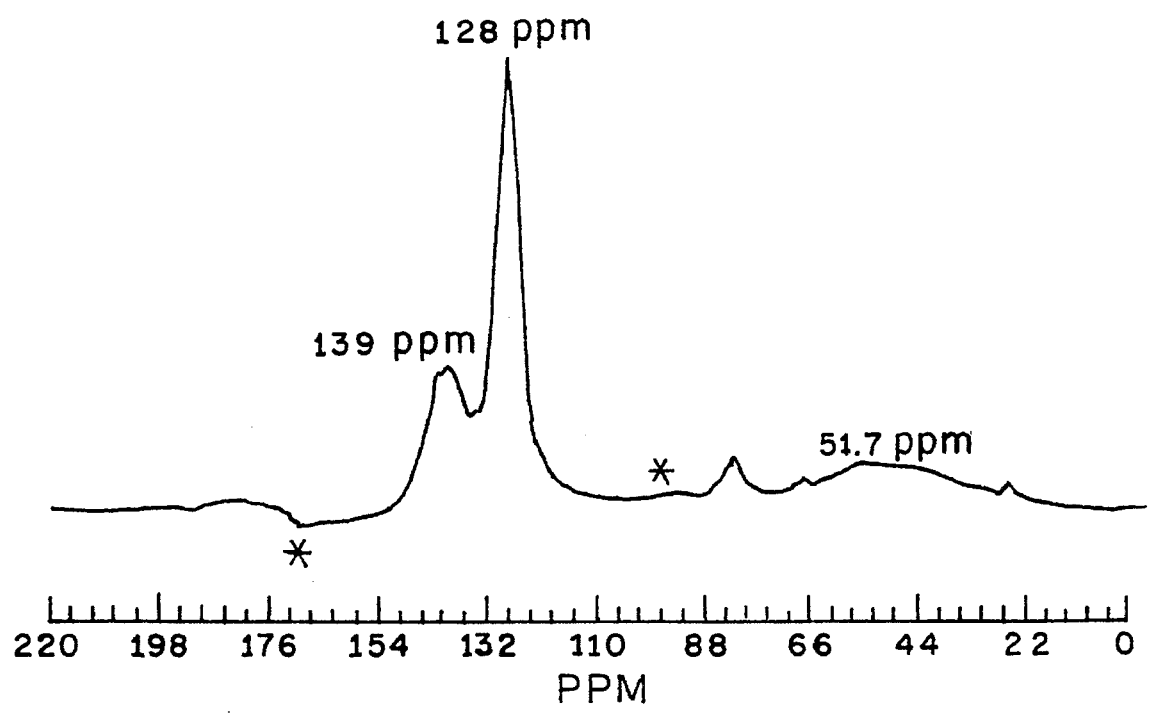
FIG. 5a shows $^{13}$C CPMAS NMR spectrum of $[PhCl]_n$, 1.
Figure 5B:
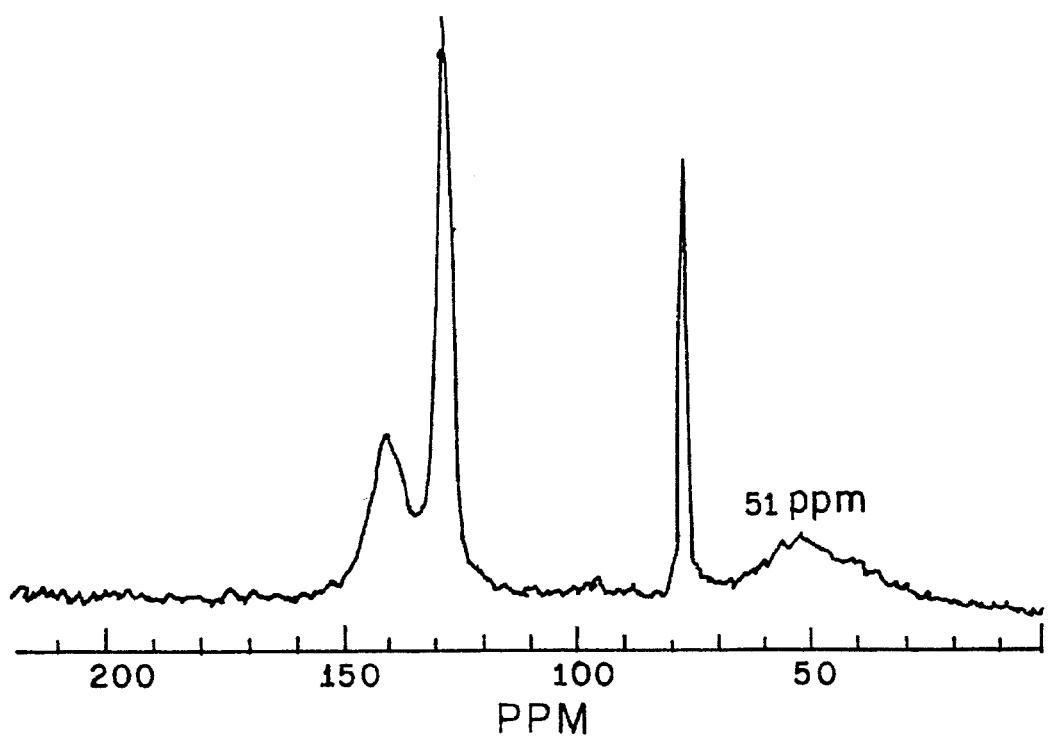
FIG. 5b shows $^{13}$C solution NMR spectrum of $[PhC]_n$ which has been 10% enriched in $^{13}$C in the backbone carbon.

Infrared (IR) spectra of 1 show a complete absence of C═C stretching bands, which are characteristic of cis-polyacetylenes and are seen in the IR spectrum of poly-(diphenylacetylene) (PDPA), the linear polymer whose empirical formula is identical to that of 1. The IR spectra also show bands consistent only with monosubstituted phenyl rings; no di- or trisubstituted phenylene-type aryl groups are present. The $^{13}$C NMR of 1 exhibits a very broad resonance ($\delta_{\nu\frac{1}{2}}$=800 Hz) centered at 51 ppm (see FIG. 5a), characteristic of quaternary carbon atoms, and no resonances other than those of the phenyl rings were detected in the vinylic carbon region, where the resonances of the backbone carbons of phenyl substituted acetylenes normally appear. The resonance at 51 ppm in the $^{13}$C NMR spectrum of 1 was enhanced when 1 was synthesized using 10 molar per cent of α,α,α-trichlorotoluene monomer which has been labeled with $^{13}$C in the α-position (see FIG. 5b). These data indicate that C═C double bonds are not primary structural features of 1, and that this polymer therefore does not adopt the linear polyacetylene structure. The presence of quaternary α-carbons as a primary structural feature and the broadness of the $^{13}C$ resonances indicate that 1 consists of a randomly constructed rigid network of tetrahedral phenylcarbyne units (see FIG. 1), in which each carbyne carbon 101 forms three single carbon-carbon bonds 102 to the network and one to the phenyl substituent 103. FIG. 1 shows two six-membered rings in the front and one five-membered ring and one eight-membered ring in the back. However, it should be understood that the continuous random network structure is characterized by a random assembly of different sized rings, including rings having 3 through 12 backbone atoms. This structure is sharply contrasted with the structure of oligomers $C_8R_8$ and $C_{20}R_{20}$. These oligomers are regularly assembled in repeating patterns and do not display the properties attributable to the continuous random network backbone.

Although spectral data indicate that the phenylcarbyne unit is the primary structural feature of 1, some indications that impurities may be present are also seen. An aliphatic C—H stretching band at 2930 $cm^{-1}$ is present in the IR spectra of 1; this is attributed to some incorporation of tetrahydrofuran (THF) into the polymer during the reductive condensation synthesis. This band is also present in the IR spectra of poly(phenylsilyne), and poly(phenylgermyne), which are also synthesized by a reductive condensation procedure in THF solution. Since no resonances attributable to incorporated THF appear in the $^1H$ NMR spectra of these polymers, and since the homopolymers give elemental analyses correct for their empirical formulas, the amount of THF incorporation into the materials must be small. A band at 3500 $cm^{-1}$, which sometimes appears in the IR spectrum of 1, may arise from absorbed water (all the phenyl-containing polymers, as well as poly(diphenylacetylene), are hygroscopic), but may also be due to C—OH sites which arise from hydrolysis of unreacted C—Cl bonds during aqueous workup. A resonance sometimes seen in the $^{13}C$ NMR spectra of 1 at δ=80 ppm (see FIG. 5a) may also indicate the presence of such sites, as this resonance has been attributed to C—OH functionalities in other carbon network polymer systems. In addition, when 1 is synthesized with addition of the trichlorotoluene monomer to the NaK alloy emulsion over time periods longer than 25 minutes, the resulting polymer displays a weak band in its IR spectra at 1642 $cm^{-1}$, indicating that C=C double bonds have formed. The intensity of this absorption increases with the time of monomer addition, suggesting that, although tetrahedral carbyne is the primary product of this reduction of an $sp^3$-hybridized monomer, the C=C double-bonded polyacetylene structure is the thermodynamic product, and may be increasingly formed with longer reaction times and sonication. Whether the regions of polyacetylene structure which appear with long reaction times are incorporated into the primary reaction product, the polycarbyne network, or form oligomers of poly(diphenylacetylene) homopolymer which are merely co-precipitated with the major product during purification, is unknown. The amount of C=C bonds incorporated as impurities into the polycarbyne backbone is small, however, because the polymers still show all the polycarbyne characteristic properties, and none of the polyacetylene characteristic properties (for example, the electronic and NMR spectra, solubilities, and reactivity). The characteristic spectral peaks of C=C bonds are seen, however, in the IR and NMR spectra of crude samples of 1, before the polymer has been purified by sequential precipitation, indicating that some oligomers containing the poly(diphenylacetylene) unit are produced by the polymerization reaction.

Poly(phenylcarbyne)'s network microstructure represents a new molecular architecture for chemically-constructed carbon materials. Other examples of carbon-based materials with designed molecular architectures include network polymers of dendrimer, arborol or hyperbranched structures, which consist of monomer units that successively branch off from a central core. Poly(phenylcarbyne) does not belong to this structural class, as it does not display the hierarchical dimensionality of branching from a multifunctional core which is characteristic of such materials. Also, all of the reported dendritic or hyperbranched types of carbon network polymers are composed of molecular units, such as aryl groups, which form the repeating units or monomers of the network. An important difference in the poly(phenylcarbyne) structure is that the repeating or network unit is a single carbon atom only, making its backbone a three-dimensional network on the atomic, rather than the molecular, scale. Fullerenes also are composed of such atomic-level carbon networks (Acc. Chem. Res. 1992, 25(3)), but the repeating units are formally $sp^2$-hybridized and π-conjugated, although the geometry adopted by many of these carbon atoms actually deviates towards tetrahedral. Carbon-based small molecules in which formally tetrahedral carbon atoms, each bearing one substituent, are joined in fused-ring structures to form polyhedral shapes, such as the cubanes ($C_8R_8$) and dodecahedranes ($C_{20}R_{20}$), can be regarded as oligomers of the poly(phenylcarbyne) structure, but 1 is the first carbon-based polymer which displays this atomic-level network backbone. Also, the carbon networks of the fullerenes, cubanes, and dodecahedranes adopt symmetrical, regular polyhedral shapes, which significantly influence their properties, while the network of 1 is randomly constructed and so irregularly shaped. The poly(phenylcarbyne) three-dimensional atomic network is similar to the three-dimensional atomic structure of solids, rather than to the polymer networks formed by molecular repeat units. The network backbone therefore displays solid-state like properties, such as great rigidity, semiconductor-like electronic behavior, and easy conversion to solid-state phases (see Section III below), more so than do organic networks formed by molecular repeat units. Such networks are often compared to, and display behavior characteristic of, micelles and membranes, while the structure and properties of poly(phenylcarbyne) are more analogous to those of small clusters of solid $sp^3$-carbon solubilized on their surfaces with aryl groups.

Figure 2A:
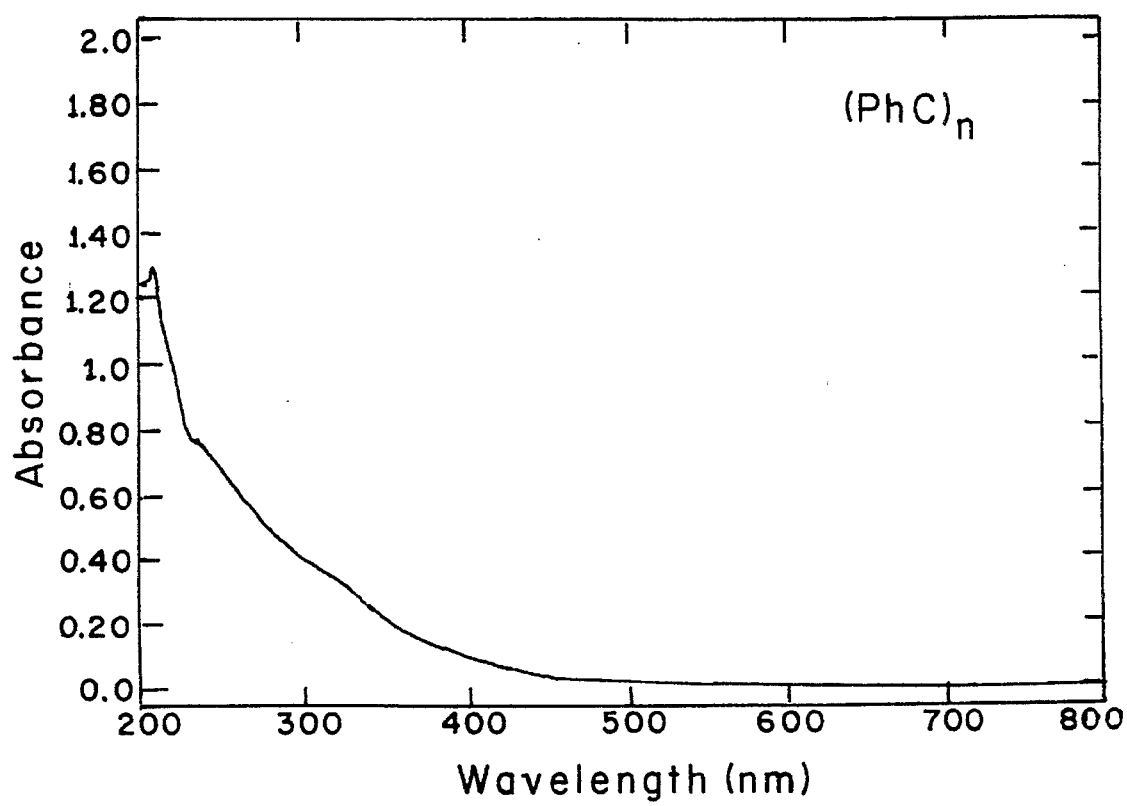
FIG. 2a shows the electronic spectrum of poly(phenylcarbyne) ($[PhC]_n$, 1) in cyclohexane solution.
Figure 2B:
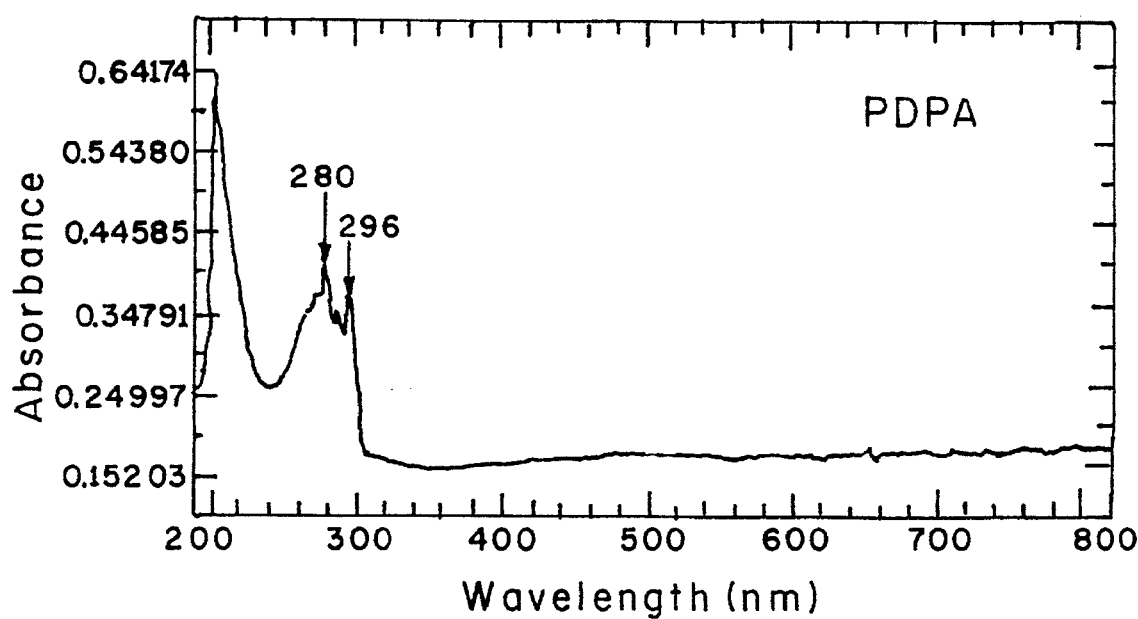
FIG. 2b shows the electronic spectrum of poly(diphenylacetylene) (PDPA) in cyclohexane solution.
Figure 6A:
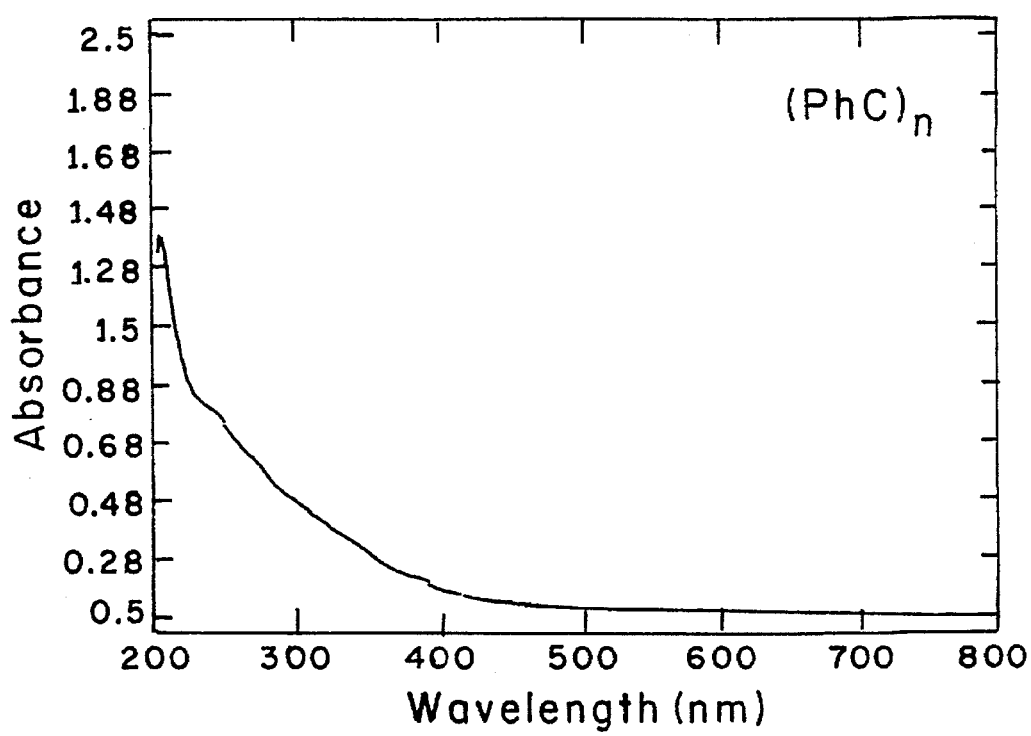
FIG. 6a shows the electronic spectrum (cyclohexane solution) of $[PhC]_n$, 1.

The physical properties of poly(phenylcarbyne) also indicate its structural similarity to inorganic network-backbone polymers, the polysilynes and polygermynes. Like the inorganic polymers, the polycarbynes are amorphous, displaying no x-ray diffraction patterns, discrete glass transition temperatures or melting points. They are air-stable in the absence of light, and can be cast from solution to form transparent films or coatings. While the electronic spectrum of poly(diphenylacetylene) (PDPA) exhibits several sharp peaks at 296 and 280 nm (see FIG. 2b) indicative of different lengths of conjugated carbon-carbon double bonds, the electronic spectrum of 1 is essentially identical to that of poly(phenylsilyne), an intense broad absorption which starts at λ<200 nm and tails down into the visible to 450 nm as shown in FIGS. 2a and 6a. This absorption band in polysilynes and germynes has been attributed to extensive σ-conjugation which extends across the three-dimensional network backbone. Polymer 1 also exhibits an intense broad fluorescence (λmax=460 nm) similar to that of the polysilynes and frequency-shifted from the emission of poly-(diphenylacetylene) (λmax=520 nm). These features of the electronic spectra of polycarbynes are analogous to those produced by long-range through-bond electron transfer via rigid non-conjugated carbon-carbon bonds in molecular species (Paddon-Row, M. N., Patney, H. K., Brown, R. S., Hook, K. N., *J. Am. Chem. Soc.*, 1981, 103, 5375), or via tunneling (Thorien, M. J.; Chang, J.; Raphael, A. L.; Bowler, B. E.; Gray, H. "Long-Range Electron Transfer in Metalloproteins", in Structure and Bonding; Springer-Verlag: Berlin, 1991, 75, 109), and are presumed to arise in the polycarbynes from hole or electron transfer through a similarly hyperconjugated carbon framework, the rigid network backbone. In these electronic properties, the polycarbynes are displaying behavior more characteristic of solids than of non-π-conjugated organic polymer networks, again demonstrating their similarly to their inorganic-backbone congeners.

Figure 6B:
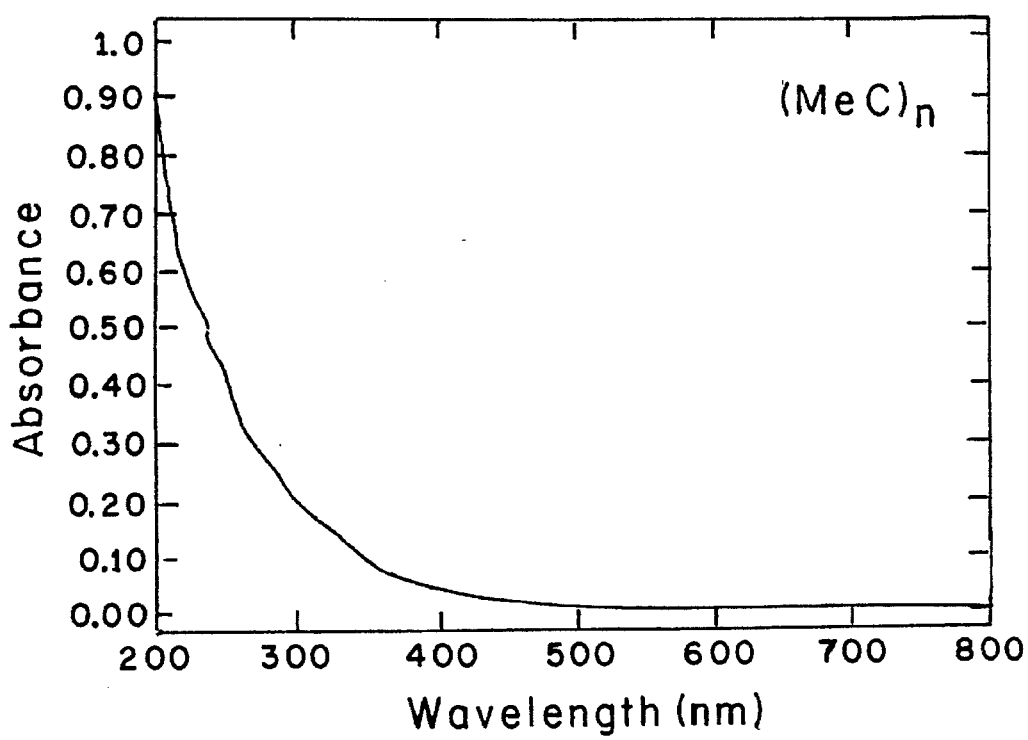
FIG. 6b shows the electronic spectrum (cyclohexane solution) of $[MeC]_n$, 2.

Like the polyacetylenes, poly(phenylcarbyne) exhibits a strong ESR signal which is characteristic in lineshape and position of carbon-centered radicals. In sterically crowded polyacetylenes, this signal is attributed to formation of radicals by the twisting of the polymer backbone to relieve steric congestion, which disrupts the carbon-carbon π-bonds. The ESR signal seen in 1 is presumed to arise from an analogous weakening or disrupting of the C—C single bonds of the network backbone in order to relieve steric strain, which again produces radicals. In contrast, poly(phenylsilyne) shows no ESR signal at all, indicating that the much longer Si—Si and Si—Ph bonds form a much less sterically crowded network, which can accommodate groups such as phenyl without disruption of the backbone's σ-bonds. A high degree of twisting of the backbone of polyacetylenes virtually destroys backbone conjugation; the position of the absorptions in the electronic spectrum of poly(diphenylacetylene) (296 and 280 nm, see FIG. 2b) indicate average conjugation lengths of only two to three carbon-carbon double bonds. In contrast, since the backbone of 1 is essentially σ-conjugated, the radicals formed upon disruption of some C—C bonds can be transferred through the three-dimensional polymer network, producing the semiconductor-like electronic absorption spectrum. That this absorption arises from the carbon network backbone, and not from any conjugated π-system formed by phenylene structures incorporated into the backbone, is demonstrated by the appearance of an almost identical absorption in poly(methylcarbyne) (see FIGS. 6a and 6b). These electronic properties are analogous to those of the silyne and germyne polymers, and indicate that these atomic-level network systems can be regarded as behaving more like small clusters of solid sp³-carbon (or silicon or germanium) solubilized on their surfaces with organic groups, rather than like carbon-based network polymers which are composed of molecular repeating units.

Figure 7:
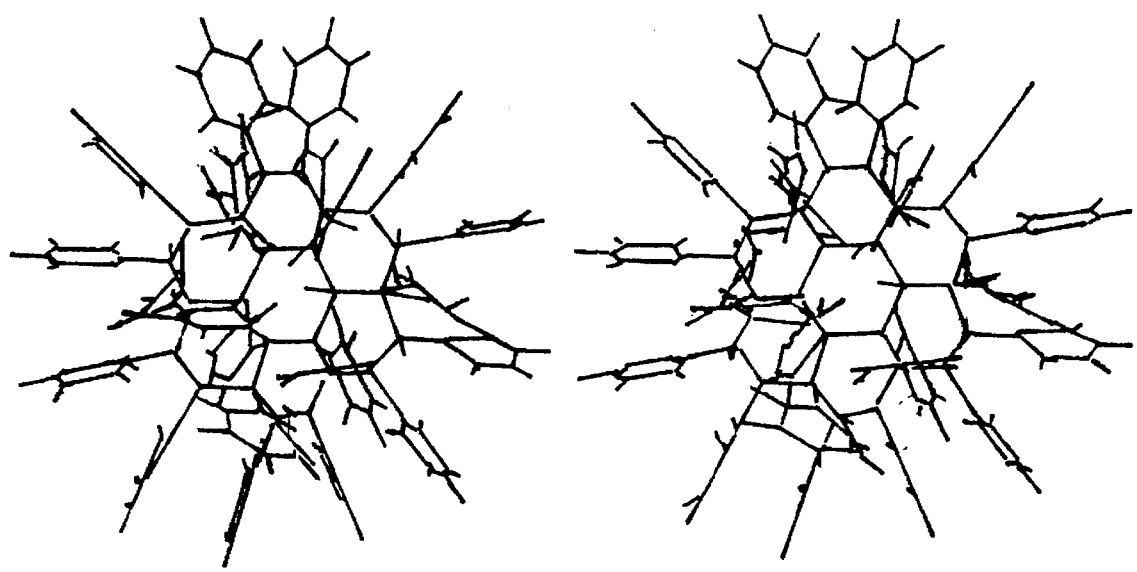
FIG. 7 shows a stereo view of a model network of poly(phenylcarbyne) having regular, six-membered rings, illustrating the packing arrangement of its phenyl substituents.

Molecular modeling has shown that the poly(phenylcarbyne) structure is indeed very sterically congested (S. A. Best, P. A. Bianconi, K. M. Merz, A Structural Analysis of Carbyne Network Polymers, submitted for publication in *J. Am. Chem. Soc.*). A series of Molecular Dynamics (MD) simulations of poly(phenylcarbyne) and related network carbyne polymers was carried out using the all-atom AMBER force field (Weiner, S. J., Kollman, P. A., Nguyen, D. T., Case, D. A., *J. Comput. Chem.*, 1986, 7, 230). Although the synthesized polymer networks consist of randomly assembled fused rings of varying sizes, the models consisted of networks of varying numbers of fused, regular, six-membered rings. Structural features of the models were analyzed by calculating average bond lengths and torsion angles. For poly(phenylcarbyne), the phenyl rings are tightly packed due to the constraints on the bond distances between carbon backbone atoms (see FIG. 7). Because the phenyl substituents are in close proximity to one another, repulsive van der Waals interactions arise and cause an increase in the amount of steric strain within the polymer backbone. Because the polymer backbone is highly rigid, the steric strain in the polymer systems results in bond cleavage and the formation of biradicals. That radical formation is driven by relief of steric strain cause by the size of the polycarbynes' substituents is also demonstrated experimentally by comparison of the ESR spectra of four different synthesized polymers, poly(phenylcarbyne), 99:01 poly(phenyl-co-hydridocarbyne), poly(methylcarbyne), and poly(phenylsilyne) (S. A. Best, P. A. Bianconi, K. M. Merz, A Structural Analysis of Carbyne Network Polymers, submitted for publication in *J. Am. Chem. Soc.*).

Polymer 1 also undergoes the photooxidation reaction (insertion of oxygen into the carbon-carbon σ-bonded network upon UV irradiation) which has been found to be characteristic of the network backbone, and which has allowed the use of polysilynes as photoresists for submicron lithography (R. R. Kunz, et al., *J. Vac. Sci. Tech. B*, 8:1820 (1990)). Exposure of 1 as a solid or solution to UV light centered at 254 nm in an ambient atmosphere results after several hours in the growth of strong C=O and C—O—C stretching bands in the IR at 1720 and 1180 cm$^{-1}$, respectively. No reaction is seen by IR when linear PDPA is irradiated under identical conditions, again indicating the existence Of a network rather than a linear backbone structure for 1. This reactivity suggests that the polycarbynes, like their silicon-based congeners, may be photopatternable and therefore useful in photolithographic processes.

In one other important respect, poly(phenylcarbyne) displays unique reactivity which can be attributed to its sp³-network backbone structure. Although both 1 and PDPA are pyrolytic precursors to carbon, in the pyrolytic conversion poly(phenylcarbyne) gives predominantly sp³-carbon phases, including diamond or diamond-like carbon, while PDPA produces principally sp²-carbon. Upon heating from room temperature to 1000° C. or to 1600° C. over 7 hours under one atmosphere of argon (Equation 2), 1 converts to a black, highly reflective, abrasive solid which contains only carbon by chemical analysis and x-ray fluorescence (%H<0.5).

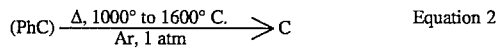

Equation 2

Figure 3:
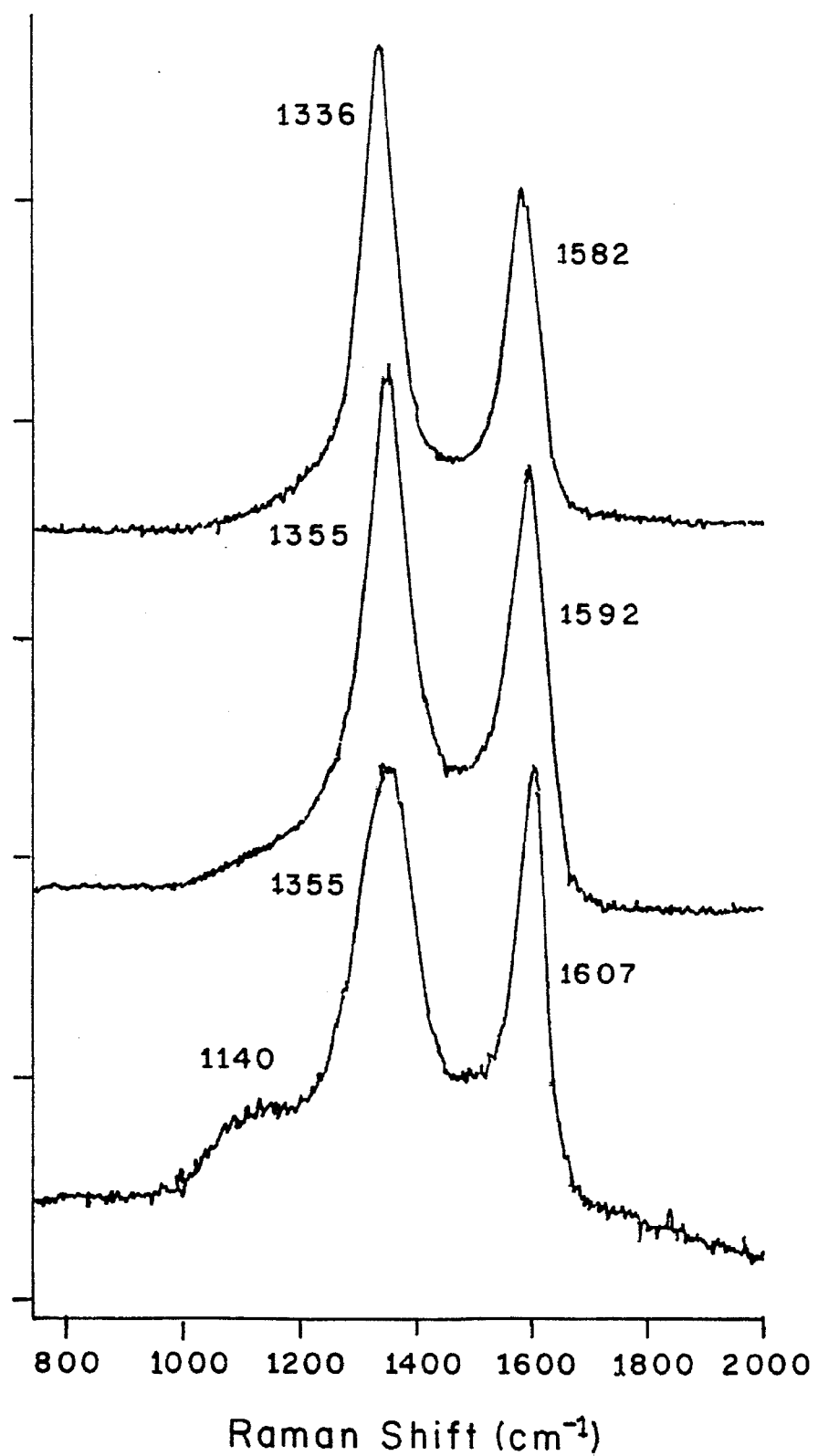
FIG. 3 shows Raman spectra of the transparent carbon produced by pyrolysis of 1 (top), the carbon produced by pyrolysis of PDPA (middle), and the black reflective carbon produced by the pyrolysis of 1 (bottom)

The carbon material produced by Equation 2 displays regions that are visibly transparent at thicknesses of 35 μm. The X-ray diffraction patterns of this carbon vary from sample to sample: peaks which correspond to peaks found in the diffraction patterns of α- and β-carbyne (R. Hayatsu, R. G. Scott, M. H. Studier, R. S. Lewis, R. S. Anders, *Science* 1980, 209, 1517) and cubic and hexagonal diamond (K. Maruyama, M. Makino, N. Kikukawa, M. Shiraishi, *J. Mater. Sci. Lett.* 11, 116, 1992), have been observed in different combinations in different samples. Under the same conditions PDPA pyrolyzes to a dull gray powder, the X-ray diffraction pattern of which shows peaks corresponding to poorly crystalline graphite and chaoite, a form of carbyne which contains a lower percentage of sp³-carbons than does α-carbyne. Raman spectra of the most transparent regions of the carbon obtained from the pyrolysis of 1 show a peak at 1336 cm$^{-1}$, indicative of diamond or predominantly sp³-bonded diamond-like carbon, as well as a peak at 1582 cm$^{-1}$ which corresponds to "nondiamond carbon" (FIG. 3, top), while Raman spectra of the carbon obtained from pyrolysis of PDPA show only $sp^2$-carbon (FIG. 3, middle). Atmospheric-pressure decomposition of poly(phenylcarbyne) at temperatures as low as 1000° C. therefore produces $sp^3$-carbon phases, some of which display transparency and hardness, as well as characteristic spectral features, approaching those of diamond. Such pyrolysis behavior is not seen in the chemically identical organic polymer PDPA, which lacks the $sp^3$-carbon network backbone which is the unique structural feature of 1.

The Raman spectra of the carbon obtained from these pyrolyses give further information about the structures of the materials. No first-order Raman bands are seen in the 2900 to 3100 $cm^{-1}$ or the 2100 to 2300 $cm^{-1}$ regions, strongly suggesting the absence of C—H bonds and C—C triple bonds in this material. The Raman spectrum of the black, reflective regions of the carbon obtained from the pyrolysis of 1 (FIG. 3, bottom) shows peaks corresponding to $sp^2$-carbon (1355 and 1607 $cm^{-1}$) and a broad shoulder centered at 1140 $cm^{-1}$, which is not seen in the carbon obtained from the pyrolysis of PDPA. Many nanocrystalline diamond samples show this feature, which is thought to arise from the effects of small crystallite size or disorder in the tetrahedral carbon network (W. A. Yarbrough, R. Messier, *Science* 247, 688, 1993). This feature has also been attributed to regions of amorphous or microcrystalline diamond, or to a precursor to crystalline diamond (R. J. Nemanich, J. T. Glass, G. Lucovsky, R. E. Shroder, *J. Vac. Sci. Technol. A* 6, 1783, 1988) Its presence here suggests that even the predominantly $sp^2$-regions of this carbon may contain some percentage of $sp^3$-hybridization.

The char yield of 1 under the above pyrolytic conditions is 40–45%, a high yield which has been found to be typical of the network backbone structure; by comparison, a char yield of only 13% is seen for the linear polyacetylene. After wet etching to remove $sp^2$-hybridized carbon (treatment with concentrated $HClO_4$ at 200° C. for five hours), the carbon product obtained from pyrolysis of 1 retains 67% of its original weight, and the carbon obtained from the pyrolysis of PDPA retains 45% of its original weight. The overall yield of "hard carbon" (i.e., carbon resistant to oxidation by $HClO_4$) obtained from pyrolysis of 1 is therefore 30%, and the yield obtained from pyrolysis of PDPA is 6%.

The difference in the amount of $sp^3$- and $sp^2$-hybridized carbon in the pyrolysis products given by the stoichiometrically identical polymers 1 and PDPA, and the formation of diamond or diamond-like carbon by the decomposition of 1, presumably are due to the presence in the backbone in 1 of the three-dimensional network of tetrahedral carbon atoms, as opposed to the $sp^2$-hybridized carbons which make up the backbone of PDPA. Upon pyrolysis, conversion of this $sp^3$-bonded carbon network to predominantly $sp^3$-bonded carbon phases is therefore favored even at atmospheric pressure. High-molecular weight carbon network polymers consisting of linear or "hyperbranched" $sp^2$-based molecules are reported to pyrolyze to give glassy (M. R. Callstrom, T. X. Neenan, R. L. McCreery, D. C. Alsmeyer, *J. Am. Chem. Soc.*, 112. 4954, 1990) or amorphous carbon (Y. H. Kim, O. W. Webster, *J. Am. Chem. Soc.*, 112, 4592, 1990), not $sp^3$-phases, again confirming that it is the already-present, all tetrahedral-carbon microstructure of poly(phenylcarbyne) that is the critical feature in allowing its facile conversion to diamond-like carbon, and not simply the presence of a carbon network. Therefore, this class of carbon-based network backbone polymers has applications as precursors to diamond or hard carbon materials at lower pressures or temperatures than some current deposition processes. The polymers' conversion properties and yield, and the quality of the diamond-like or hard carbon products obtained from them, can be optimized by the use of side-groups other than phenyl and by more sophisticated processing techniques than simple pyrolysis. The easy processibility of these soluble, film-forming polymers is advantageous in coating substrates or in forming submicron features by high-resolution laser pyrolysis. Thermal gravimetric analysis shows that the thermal decomposition of 1 begins at 200° C. and is complete at 450° C., having reached a constant weight of 40–45% of the initial. Annealing to 1000° C. or 1600° C. improves the transparency of the carbon product. Though the upper limit of the carbon product's hardness has not been established, we have observed that it easily scratches agate (hardness 6–7 Mohs). It is therefore much harder than graphite (0.5–1 Mohs).

II. Synthesis of the Polymers

In synthesizing carbon-based analogues of inorganic network polymers, the much greater strength of C=C bonds over multiple bonds between inorganic elements was considered. Because of the strength of the C=C bonds, a synthesis procedure would be expected to yield a polyacetylene structure with C=C bonds. Unexpectedly, the synthesis procedure reported herein produced polymers having a continuous random network backbone without significant amounts of C=C bonds.

Carbon polymers containing the tetrahedrally-hybridized carbyne unit (CR) were previously unknown, although many examples of oligomers of such units have been reported. All other polymers of $[CR]_n$ stoichiometry adopt the polyacetylene structure, comprised of linear backbones of alternating C—C and C=C bonds. These polymers, however, are without exception synthesized by the polymerization of acetylene monomers, in which the carbon atoms are sp-hybridized. The invention is derived, in part, from the inventor's discovery that rapid polymerization of monomers in which the carbon atoms were $sp^3$-hybridized allows assembly of these atoms into tetrahedral arrays, or network backbones.

The invention is also derived, in part, from the inventor's discovery of the synthesis of silyne/carbyne network copolymers, and metal-containing polycarbynes. The syntheses involve addition of varying ratios of $RSiCl_3$ and $PhCCl_3$ monomers to an ultrasonically irradiated emulsion of THF and NaK (see Equation 3 below), and reductive condensation of varying ratios of $PhCCl_3$ with $CpTiCl_3$ and $Cp*HfCl_3$ (see Equation 6 below).

As described below, the syntheses of the first $[CR]_n$ network polymers, or polycarbynes, and of copolymers containing the carbyne unit, were unexpectedly achieved by reductive condensation of $RCCl_3$ and similar monomers using ultrasonically generated THF NaK alloy emulsions. This result is particularly unexpected given the explosive nature of tri-halogen carbides when reduced by metals such as Na or K. The new polymers are soluble in organic solvents and can be cast to form transparent films or coatings. All chemical and spectroscopic data indicate that the polycarbynes and their copolymers with inorganic and metallic elements are primarily composed of $sp^3$-hybridized alkyl or arylcarbyne units assembled via C—C single bonds into irregular networks. The atomic-level carbon network backbone confers unusual properties on the polymers, including, in the case of 1, facile thermal decomposition to form diamond or diamond-like carbon phases.

The number and type of other metals or elements which can be incorporated into the polymer backbone include but is not limited to silicon, germanium, tin, lead, other Group 13 through Group 16 elements, Group 4 metals and Lanthanides (typically cerium, praseodymium, neodymium, promethium, samarium, europium, gadolinium, terbium, dysprosium, holmium, erbium, thulium, ytterbium, lutetium). Lanthanides, boron, nitrogen, phosphorous and zirconium have been incorporated into silyne polymers.

When these other elements are incorporated, the R group on the silyne or carbyne monomers does not necessarily change, and the R groups discussed above can be used. The sidegroup (if any) on other inorganic elements incorporated into the backbone could be any of the previously-mentioned R groups, heteroatom-based ligands, or nothing at all. For example, boron has been incorporated from $BBr_3$ starting material. When incorporated into the polymer, the $Br^-$ ions are removed, and the B atoms are incorporated without any substituent. The atoms of other elements incorporated into the backbone are not necessarily tetrahedrally hybridized, but since they form such weak double bonds they are not $sp^2$-hybridized either. Each of these elements has characteristic bonding and hybridization, which they adopt when incorporated into the polymer backbones. The degree of polymerization when other atoms or elements are in the backbone depends primarily upon the components of the remainder of the backbone. Therefore, the lower limit of "n" would be approximately 8, and the upper limit of "n" at least 1,200 for polymers containing other metals or elements.

Atoms, including carbon, can be incorporated into the backbone so that they are connected to the backbone by four single bonds and thus these atoms do not have an R substituent. For example, $[(RC)_x(C)_y]_n$ can be produced from $xRCCl_3$ and $yCCl_4$ by following the reduction procedures described below. Other inorganic or metal atoms could also be incorporated without R substituents to produce $[(RC)_x(M)_y]_n$, where M is silicon, germanium, titanium, other metal atoms, or any Group 13 through Group 16 element.

All syntheses described below were performed in an inert atmosphere glovebox equipped with a Heat Systems-Ultrasonic Inc. W-485 ultrasonic processor and immersion horn with a ¼" titanium tip. Solvents used in the syntheses were Aldrich anhydrous grade, and were distilled from sodium benzophenone prior to use. Liquid 1:1 mole ratio NaK alloy was prepared in the glovebox by adding solid potassium to an equimolar amount of molten sodium. α,α,α-trichlorotoluene, 1,1,1-trichloroethane (Aldrich), phenyltrichlorosilane, n-butyltrichlorosilane (Silar), pentamethylcyclopentadieynlhafnium trichloride (Sirere), cyclopentadienyltitanium trichloride (Aldrich) and Grignard reagents (Aldrich) were obtained from commercial sources and used as received. $^{13}C$-enriched α,α,α-trichlorotoluene was synthesized by MSD, Inc. Solution state NMR spectra were recorded at room temperature as saturated $CDCl_3$ solutions using a Bruker WP-200 spectrometer (50 MHz for $^{13}C$). Solid state $^{13}C$ cross polarization magic angle spinning (CPMAS) spectra were recorded on a Chemagnetics CMX-300 spectrometer resonating at 74.78 MHz for $^{13}C$. Infrared spectra were recorded on a IBM FTIR-32 instrument. Electronic spectra were recorded on a Hewlett-Packard 8450A UV/vis spectrophotometer. Gel permeation chromatography (GPC) of polycarbynes was performed with a Waters 410 GPC/RI instrument equipped with a refractive index detector and three Waters ultrastyragel columns with pore sizes of $10^3$, $10^4$, and 500 Å. The GPC was interfaced with a NEC Powermate 386 computer with Millipore Millenium 2010 software. All GPC samples were run in a tetrahydrofuran (THF) flow of 1.0 ml/min at 35° C. and are reported versus polystyrene standards. ESR spectra were measured on a Varian E-Line Model EPR spectrometer at 9 GHz, with a modulation frequency of 100 kHz. Elemental analyses were obtained by combustion at 1600° C. in the presence of $V_2O_5$ from Galbraith Laboratories, Nashville, Tenn.

Because the GPC molecular weights of the polymers reported below were determined using linear polystyrene standards, the absolute value of the molecular weights are probably underestimated, as is seen in other network polymer systems, and should be regarded as an estimate and a lower limit only.

A. Synthesis of Poly(phenylcarbyne)

Poly(phenylcarbyne), [PhC]n (1). The synthesis of poly(phenylcarbyne) was performed in accordance with Equation 1.

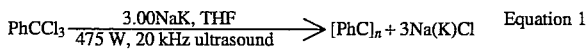

$$PhCCl_3 \xrightarrow[475 \text{ W}, 20 \text{ kHz ultrasound}]{3.00 \text{NaK, THF}} [PhC]_n + 3Na(K)Cl \quad \text{Equation 1}$$

NaK alloy (50:50 mol %, 9.3 g, 300 mequiv) in 250 mL of THF (tetrahydrofuran) was ultrasonically irradiated at full power for three minutes (Caution: The extremely pyrophoric nature of NaK alloy emulsions, combined with the greater likelihood of glassware breaking under ultrasonic irradiation, requires that this procedure preferably be performed in an inert atmosphere glovebox). A solution of α,α,α-trichlorotoluene (10.65 mL, 100 mmol) in 20 ml of pentane was added dropwise to the reaction mixture over 20 minutes while sonication was continued. After the addition was complete, ultrasonic irradiation was continued for 20 minutes, with THF added as needed to replace that lost by evaporation. The reaction mixture was then removed from the drybox to a shielded hood, and 250 mL of water were added, after which the organic layer was separated from the aqueous layer. The organic layer was concentrated to 50 mL in vacuum. Addition of 200 mL of methanol gave a tan precipitate which was collected by filtration and purified by reprecipitation with ethanol from a THF solution, giving 2.23 g (25%) of poly(phenylcarbyne) (1): $^1H$ NMR δ7.4 (br, $C_6H_5$); $^{13}C\{^1H\}$ NMR δ140, 125 (br, $C_6H_5$), 51 (br, $CC_6H_5$); δIR (KBr pellet, $cm^{-1}$): 3055(s), 3024(s), 2930(m), 1946(m), 1890(m), 1811(m), 1600(s), 1491(m), 1444(s), 1180(s), 1175(s), 1050(m), 900(w), 750(s), and 670(s); GPC (THF versus polystyrene): $M_w$=4000, $M_n$=3077, polydispersity=1.3. Electronic spectrum (cyclohexane): onset at 450 nm, increasing gradually in intensity with decreasing wavelength to 200 nm. Emission spectrum (cyclohexane, excitation wavelength=300 nm) λmax=460 nm. Anal.: Calc.for $C_7H_5$: C, 94.34; H, 5.66; Found: C, 94.95; H, 6.13. ESR (9.1 GHz, solid): g=2.005.

B. Synthesis of Polymethylcarbyne)

Poly(methylcarbyne), [MeC]n (2). The synthesis of poly(methylcarbyne) was performed in accordance with Equation 4.

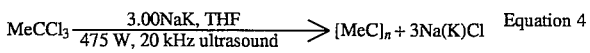

$$MeCCl_3 \xrightarrow[475 \text{ W}, 20 \text{ kHz ultrasound}]{3.00 \text{NaK, THF}} [MeC]_n + 3Na(K)Cl \quad \text{Equation 4}$$

1,1,1-Trichloroethane (10 mL, 100 mmol) was reduced with NaK alloy (9.3 g, 300 mequiv) following the same procedure that was used to prepare 1. After complete addition of the monomer and subsequent sonication, methanol (10 mL) was added to the reaction mixture while sonication was continued for 10 minutes. A vigorous reaction indicated that much of the NaK remained unreacted. The reaction mixture was then removed from the drybox to a shielded hood, where 200 mL of water were added. The red/brown organic layer was separated from the aqueous and concentrated in vacuum to 20 mL. Addition of 200 mL of methanol gave 95 mg (3.5%) of poly(methylcarbyne) (2) as a tan solid after filtration. $^{13}C$ NMR of the organic layer showed unreacted or partially reduced monomer as the only side products. Spectral data for 2: $^1$H NMR δ1.0 (br, CH$_3$); IR (neat film on KBr, cm$^{-1}$) 2967(s), 2930(s), 2851(s), 1638(w), 1453(m), 1375(s), 1258(vs), 1096(w), 1024(w), 850(w), 752(vw); GPC (THF versus polystyrene): M$_w$=8096, M$_n$=4425, polydispersity=1.85. Electronic spectrum (cyclohexane): onset at 400 nm, increasing gradually in intensity with decreasing wavelength to 200 nm. Anal. Calc. for C$_2$H$_3$: C, 88.99; H, 11.11. Found: C, 64.96; H, 9.28.

The reaction proceeded only to a small extent; the yield of soluble, polymeric product was only 3.5%, and the only side products observed were unreacted or partially reduced monomer. The amount of 2 obtained was too little to observe $^{13}$C NMR spectra, but GPC showed it to be polymeric, and its IR and $^1$H NMR were consistent with those seen for other network polymers. Significantly, the electronic spectrum of 2 displays the characteristic network polymer absorption, confirming the presence of the carbyne network backbone (see FIGS. 6a and 6b), rather than the absorptions characteristic of polydialkylacetylenes (T. Masuda, et al., *Polym. J.* 14:371 (1982)). The presence of this absorption in an alkyl-substituted polycarbyne demonstrates that the apparent conjugation of these polymers' backbones does not arise from an extended π-system which might be formed during the reductive condensation of aryl-substituted monomers by reaction at the phenyl rings to give phenylene structures in the backbone.

The IR spectra of 2 show a band at 1638 cm$^{-1}$, indicative of C=C double bonds, regardless of addition time of the monomer during the synthesis. The greater tendency for formation of the polyacetylene-type structure that is seen with this monomer is quite probably due to the relief of steric strain in the linear structure upon moving from the large phenyl substituent to the smaller methyl group. Similarly, the GPC weight-average molecular weight of 2 (8096 daltons) is approximately twice that of 1 (4000 daltons), demonstrating the increase in degree of polymerization with decreasing steric bulk of substituent which was found to be the critical factor in determining the molecular weight of the inorganic network polymers.

With the inorganic network backbone polymers, it has been demonstrated that a substituent which extends at least three atoms out from the polymer backbone is necessary to solvate these networks (P. A. Bianconi et al., *Macromolecules* 22:1697 (1989)); for example, [MeSi]$_n$ (Me=methyl) and [EtSi]$_n$ (Et=ethyl) are insoluble materials, and [n-PrSi]$_n$ (n-Pr=n-propyl) is only marginally soluble. Carbon-carbon single bonds are much shorter than those between inorganic elements (1.54 Å vs 2.34 Å for Si—Si single bonds). The inventor has demonstrated that polycarbynes of the same degree of polymerization form smaller networks solvated by shorter substituent groups by the synthesis of poly(methylcarbyne), 2, by the reductive condensation of 1,1,1-trichloroethane.

C. Synthesis of Poly(phenyl-co-methylcarbyne) 75:25 Poly(phenyl-co-methylcarbyne), [(PhC)$_{0.75}$(MeC)$_{0.25}$]$_n$ (3). The synthesis of poly(phenyl-co-methylcarbyne) was performed in accordance with Equation 5.

0.75 PhCCl$_3$ +                                           Equation 5

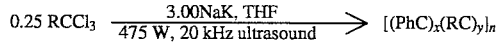

R = Me, H

NaK alloy (50:50 mol %, 9.3 g, 300 mequiv) in 225 mL of THF was ultrasonically irradiated at full power for three minutes. A solution of α,α,α-trichlorotoleune (10.5 mL, 75 mmol) in 25 ml of pentane, and a solution of 1,1,1-trichloroethane (2.5 mL, 25 mmol) in 25 ml of pentane were added dropwise simultaneously over 18 minutes with sonication, and sonication was continued for 10 minutes after the additions were complete. Methanol (100 mL) was added, and a vigorous reaction indicated that some NaK remained unreacted. Following the addition of the methanol, the red-brown reaction mixture was removed from the drybox, insoluble material was removed by filtration, and purification was carried out as described for 1. This procedure gave 2.45 g (33%) of [(PhC)$_{0.75}$(MeC)$_{0.25}$]$_n$ (3) as a tan solid: $^1$H NMR δ7.2 (br, C$_6$H$_5$), 1.2 (br, CH$_3$); integration gives an empirical formula of [(PhC)$_{0.88}$(MeC)$_{0.12}$]$_n$; IR (KBr pellet, cm$^{-1}$) 3443(w), 3061(s), 3024(s), 2926(m), 1950(m), 1890(m), 1807(m), 1599(s), 1492(vs), 1444(vs), 1260(s), 1074(s), 1030(s), 758(s), 698(s); electronic spectrum (cyclohexane): onset at 500 nm, increasing gradually with decreasing wavelength to 200 nm; GPC (THF vs. polystyrene) M$_w$=6777, M$_n$=4912, polydispersity=1.37. Anal.: Calc. for (PhC)$_{0.75}$(MeC)$_{0.25}$: C, 93.88; H, 6.12; Found: C, 72.12; H, 6.19.

Figure 4A:
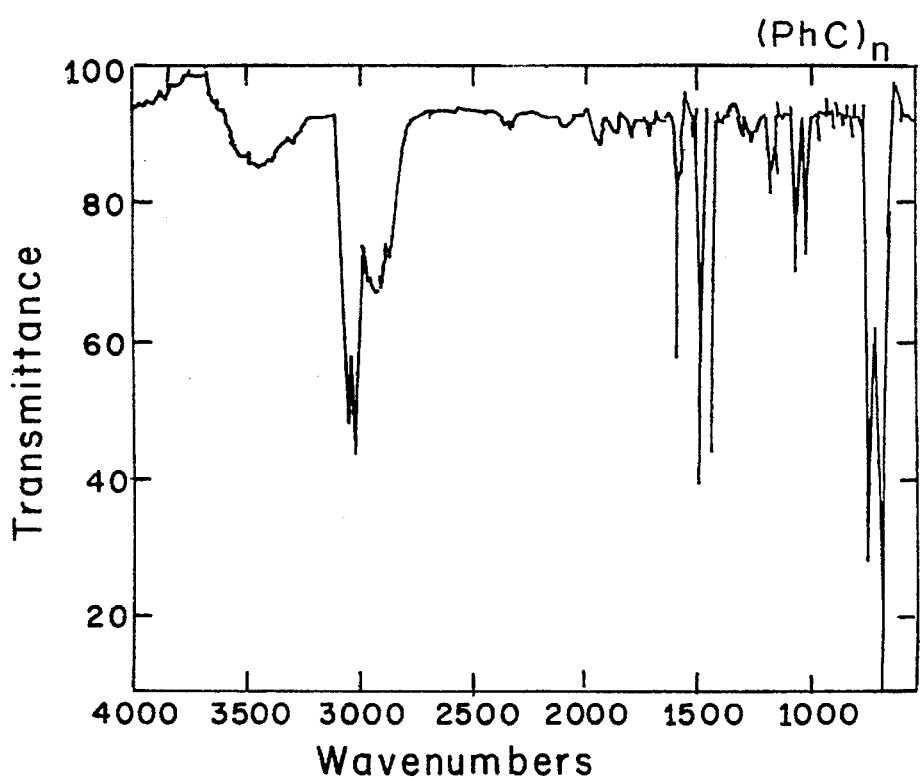
FIG. 4a shows the IR spectrum of $[PhC]_n$, 1.
Figure 4B:
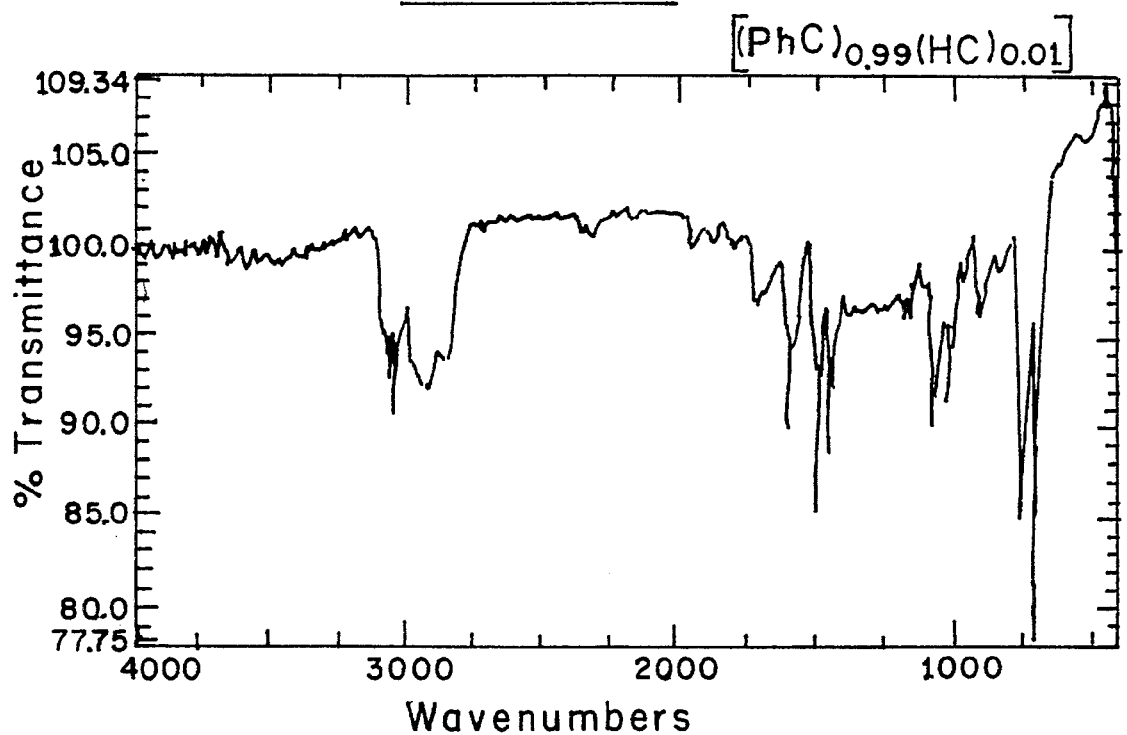
FIG. 4b shows the IR spectrum of $[(PhC)0.99(HC)0.1]_n$, 6.

For R=Me in equation 5, [(PhC)$_x$(MeC)$_y$]$_n$ was produced, and for R=H in Equation 5, [(PhC)$_x$(HC)$_y$]$_n$ (see Section F. below) was produced. In both cases, soluble polymeric materials were isolated as tan powders; each reaction also produced some insoluble crosslinked material, the amount of which increased upon increasing the percentage of the MeCCl$_3$ or HCCl$_3$ monomers. For monomer ratios of 75:25 PhCCl$_3$ to MeCCl$_3$ and 90:10 PhCCl$_3$ to HCCl$_3$, yields of soluble polymers ranged from 12 to 33%. IR spectra show bands at 1640 and 1732 for the MeCCl$_3$ and HCCl$_3$-derived copolymers, respectively (see FIG. 4b); the intensities of these bands increase with increasing incorporation of MeC or HC units, again attributable to increased polyacetylene structure formation with increasing relief of steric strain. Similarly, the GPC weight-average molecular weights of the PhC/MeC copolymers are intermediate between those of the two homopolymers. Electronic spectra of the copolymers show the broad absorption band characteristic of the network backbone; also, the $^{13}$C NMR spectrum of a 90:10 PhC/HC copolymer which was prepared using $^{13}$C-enriched HCCl$_3$ shows a strong, broad resonance in the quaternary carbon region (20–80 ppm), indicative of the carbyne structure.

Co-reduction of 75% PhCCl$_3$ with 25% MeCCl$_3$ gives a copolymer which, by the hydrogen elemental analysis, has an empirical formula of [(PhC)$_{0.75}$(MeC)$_{0.25}$]$_n$ (3). Integration of the CH$_3$ resonance at 1.2 ppm in the $^1$H NMR spectrum of 3 with the phenyl proton resonance at 7.2 ppm gives an empirical formula of [(PhC)$_{0.88}$(MeC)$_{0.12}$]$_n$. This underestimation of the methyl protons in the $^1$H NMR integration is consistent with the observed increase in rigidity and concomitant broadening and decrease in signal intensity which is seen in the NMR resonances of substituent carbon and hydrogen atoms of the polysilynes as the substituent atoms become closer to the rigid network backbone. Similarly, co-reduction of 90% PhCCl$_3$ with 10% HCCl$_3$ gives a polymer which, by proton integration, has an empirical formula of [(PhC)$_{0.99}$(HC)$_{0.01}$]$_n$ (6, see F. below), which the hydrogen elemental analysis shows is an underestimation of the amount of HC units incorporated. Taking the empirical formulas given by integration as lower limits, the amount of MeC or HC units incorporated into copolymer with PhC is masonably close to that introduced in the synthesis.

D. Synthesis of Poly(phenylcarbyne-co-phenylsilyne) 80:20Poly(phenylcarbyne-co-phenylsilyne), $[(PhC)_{0.08}(PhSi)_{0.02}]_n$ (4).

The synthesis of poly(phenylcarbyne-co-phenylsilyne) was performed in accordance with Equation 3.

$$0.75\ PhCCl_3\ + \qquad \text{Equation 3}$$

$R = Ph,\ n\text{-}Bu$ $\alpha,\alpha,\alpha$-Trichlorotoluene (10.5 mL, 75 mmol) and phenyltrichlorosilane (3.9 mL, 25 mmol) were reduced with NaK (9.3 mL, 300 mequiv) following the same procedure that was used to prepare 3. The product was purified by sequential precipitation from THF solution with water, methanol and ethanol. This procedure gave 3.90 g (42%) of $[(PhC)_{0.80}(PhSi)_{0.02}]_n$ (4) as a yellow-orange powder: $^1$H NMR $\delta$7.2 (br, $C_6H_5$); $^{13}$C(CPMAS) 135, 125 (br,$C_6H_5$), 65, 40 (br, $CC_6H_5$); IR (KBr pellet, cm$^{-1}$) 3036(s), 2942(s), 2937(m), 1950(m), 1870(m), 1595(s), 1484(s), 1443(m), 1419(s), 1260(m), 1114(m), 1067(m), 1020(m), 990(m), 732(s), 690(vs); GPC (THF versus polystyrene): $M_W$=11,381, $M_n$=4833, polydispersity=2.3; electronic spectrum (cyclohexane): onset at 450 nm, increasing gradually with decreasing wavelength to 200 nm. Anal.: Calc. for $(PhC)_{0.08}(PhSi)_{0.02}$: C, 88.50; H, 5.42; Si, 6.10; Found: C, 76.04; H, 5.43; Si, 6.10.

The synthesis of copolymers of PhCCl$_3$ with n-butylSiCl$_3$ and with PhSiCl$_3$ in 75:25 ratios were accomplished by this method. The polymers were both obtained as soluble yellow/orange powders in yields of 20–40%, with empirical formulas of $[(PhC)_{0.80}(PhSi)_{0.20}]_n$ (4) and $[(PhC)_{0.78}(n\text{-}BuSi)_{0.22}]_n$ (5, see E. below). Insoluble, crosslinked material and low-molecular weight oligomers were the only other products. In both these polymers (and in virtually all those containing the carbyne unit) elemental analyses were significantly low in carbon. Since we have discovered that carbyne-backbone polymers are efficient pyrolysis precursors to diamond or diamond-like carbon, a significant portion of the carbyne backbone may be converted to hard, oxidation-resistant carbon during combustion analysis, resulting in the low carbon values obtained. Similarly low values are seen in the combustion analyses of many molecular and polymer precursors to refractory ceramics (Young, R. S. Analyst 1982, 107, 721). Empirical formulas were therefore calculated from hydrogen and silicon analysis percentages. $^1$H NMR integration gave an empirical formula of $[(PhC)_{0.61}(n\text{-}BuSi)_{0.39}]_n$ for 5, but the inaccuracy of integration of the very broad peaks typical of network-backbone polymers makes the analytically-derived formula more probable.

IR spectra of 4 and 5 show no bands at 1640–1655 cm$^{-1}$, which typically arise from cis-C=C double bonds in the backbones of polyacetylenes. In the IR spectra of both polymers, bands characteristic of mono-substituted phenyl rings (1950, 1870–1850, 1718, and 750–730, 690 cm$^{-1}$) were seen, and no bands typical of phenylene structures (730 to 830 cm$^{-1}$) are present. The IR spectra therefore suggest that in both 4 and 5, the [PhC] units are present as tetrahedral carbynes rather than as sp$^2$-hybridized species, and that no crosslinking or reaction at the phenyl substituents has occurred. This is confirmed by the electronic spectra of the copolymers, which are virtually identical to those of polysilyne homopolymers, indicating that the network backbone structure is present. The $^{13}$C CPMAS NMR spectrum of 5 shows broad resonances between 40 and 65 ppm, in addition to the phenyl resonances at 125 and 135 ppm, which are typical of quaternary carbons (as seen, for example, in cubanes and dodecahedranes). All spectral data on 4 and 5, therefore, indicate that these materials are copolymers of silyne and carbyne units, each linked by three single bonds into a network backbone.

E. Synthesis of Poly(phenylcarbyne-co-n-butylsilyne) 78:22 Poly(phenylcarbyne-co-n-butylsilyne), $[(PhC)_{0.78}(n\text{-}BuSi)_{0.22}]_n$ (5). The synthesis of poly(phenylcarbyne-co-n-butylsilyne) was also performed in accordance with Equation 3.

$$0.75\ PhCCl_3\ + \qquad \text{Equation 3}$$

$R = Ph,\ n\text{-}Bu$ $\alpha,\alpha,\alpha$-Trichlorotoluene (10.5 mL, 75 mmol) and n-butyltrichlorosilane (4.1 mL, 25 mmol) were reduced with NaK (9.3 mL, 300 mequiv) following the same procedure used to prepare 3. The product was purified by sequential precipitation from THF solution with water, methanol and ethanol. This procedure gave 2.09 g (22%) of $[(PhC)_{0.78}(n\text{-}BuSi)_{0.22}]_n$ as a yellow powder: $^1$H NMR $\delta$7.2 ($C_6H_5$), 1.16, 0.85 ($C_4H_9$); integration gives the empirical formula of $[(PhC)_{0.61}(n\text{-}BuSi)_{0.39}]_n$; IR (KBr pellet, cm$^{-1}$) 3024(s), 2924(s), 1947(m), 1850(m) 1718(m), 1598(s), 1493(vs), 1445(s), 1376(m), 1193(m), 1078(m), 1026(s), 963(s), 882(m), 757(s), 698(vs); GPC (THF versus polystyrene): $M_W$=9298, $M_n$=5830, polydispersity=1.59; electronic spectrum (cyclohexane): onset at 400 nm, increasing gradually with decreasing wavelength to 200 nm. Anal.: Calc. for $(PhC)_{0.777}(n\text{-}BuSi)_{0.223}$: C, 87.11; H, 6.24; Si, 7.16; Found: C, 74.70; H, 7.24; Si, 7.11.

F. Synthesis of Poly(phenylcarbyne-co-hydridocarbyne) 99:1 Poly(phenyl-co-hydridocarbyne), $[(PhC)_{0.99}(HC)_{0.01}]_n$ (6). The synthesis of poly(phenylcarbyne-co-hydridocarbyne) was performed in accordance with Equation 5.

$$0.75\ PhCCl_3\ + \qquad \text{Equation 5}$$

$R = Me,\ H$ $\alpha,\alpha,\alpha$-Trichlorotoluene (9.7 mL, 90 mmol) and chloroform (0.6 mL, 10 mmol) were reduced with NaK (9.3 mL, 300 mequiv) following the same procedure used to prepare 3. The reaction mixture was purified by sequential precipitation from THF solution with water, methanol and ethanol. This procedure gave 1.04 g (12%) of $[(PhC)_{0.99}(HC)_{0.01}]_n$ (6) as a tan powder: $^1$H NMR $\delta$7.2(br, $C_6H_5$), 2.0 (CH); integration gives an empirical formula of $[(PhC)_{0.99}(HC)_{0.01}]_n$; $^{13}$C {$^1$H}NMR (10% 13C-enriched at CH) $\delta$128, 114 ($C_6H_5$), 38 (CH); IR (KBr pellet, cm$^{-1}$) 3060(s), 3025(s), 2931(m), 1950(m), 1878(m), 1805(m), 1732(w), 1595(s), 1490(s), 1443(m), 1155(s), 1114(s), 1067(s), 1025(s), 755(s), 690(vs); GPC (THF versus polystyrene): $M_W$=5898, $M_n$=4168, polydispersity=1.41; electronic spectrum (cyclohexane): onset at 400 nm, increasing gradually with decreasing wavelength to 200 nm. Anal.: Calc. for $(PhC)_{0.99}(HC)_{0.01}$: C, 94.38; H, 5.62; Found: C, 86.45; H, 6.42.

G. Synthesis of Poly(phenylcarbyne-co-cyclopentadienyltitanium)

98:2Poly(phenylcarbyne-co-cyclopentadienyltitanium), $[(PhC)_{0.98}(CpTi)_{0.02}]_n$ (7). The synthesis of poly(phenylcarbyne-cocyclopentadienyltitanium) was performed in accordance with Equation 6.

0.75 PhCCl$_3$ + 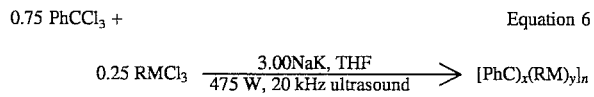 [PhC)$_x$(RM)$_y$]$_n$  Equation 6

R = Cp, M = Ti
R = Cp*, M = Hf

α,α,α-Trichlorotoluene (7.99 g, 75 mmol) and cyclopentadienyltitanium trichloride (5.6 g, 25 mmol, in 10 mL THF) were reduced with NaK (9.3 mL, 300 mequiv) following the same procedure used to prepare 3. After complete addition of the monomers and subsequent sonication, water (200 mL) was added to the reaction mixture in a shielded hood, and the organic layer was separated from the aqueous. Addition of 200 mL of methanol to the organic layer gave a tan precipitate, which was collected by filtration and triturated with THF. This solution was filtered to remove 3.25 g of an insoluble brown solid. Addition of ethanol to the filtrate and re-filtration gave 1.00 g (11%) of [(PhC)$_{0.98}$(CpTi)$_{0.02}$]$_n$ (7) as a yellow powder: $^1$H NMR δ7.2 (br, C$_6$H$_5$), 3.6 (br, C$_5$H$_5$); integration gives the empirical formula [(PhC)$_{0.97}$(CpTi)$_{0.03}$]$_n$; $^{13}$C{$^1$H} NMR δ140, 125 (br, C$_6$H$_5$), 41 (br, CC$_6$H$_5$); $^{13}$C CPMAS NMR δ 140, 128 (br, C$_6$H$_5$), 116 (br, C$_5$H$_5$); IR (KBr pellet, cm$^{-1}$) 3421(w), 3061(s), 3024(s), 2908(w), 1950(m), 1866(m), 1726(m), 1620(s), 1508(vs), 1450(s), 1145(s), 1130(s), 1074(s), 1030(s), 942(m), 758(s), 698(s); GPC (THF versus polystyrene): M$_w$=3327, M$_n$=2600, polydispersity=1.27; electronic spectrum (cyclohexane): onset at 450 nm, increasing gradually with decreasing wavelength to 200 nm, shoulder at 248 nm. Anal.: Calc. for (PhC)$_{0.976}$(CpTi)$_{0.024}$: C, 93.14; H, 5.58; Ti, 1.28; Found: C, 84.88; H, 6.12; Ti, 1.27.

In each case of R=C$_p$, M=Ti; R=C$_p$*, M=Hf in Equation 6, soluble polymeric materials were isolated as tan powders; the reactions involving the titanium species also produced some insoluble crosslinked material, although the Hf reactions gave soluble oligomeric species as the only side products. For monomer ratios of 75:25 PhCCl$_3$ to CpTiCl$_3$ or Cp*HfCl$_3$, yields of soluble polymers ranged from 7 to 11% (for the calculated empirical formulas). Because of the very great steric bulk of the Cp and Cp* substituents, it was not clear that any metal species would be incorporated, or that any high molecular weight material would be obtained. Also, the extremely reducing conditions under which the polymerizations are carried out may have reduced the metal-containing species to colloidal metal before any could be incorporated into the polymers. The yields of soluble polymeric material were lower for reactions which involved the far bulkier Cp*Hf unit as opposed to the CpTi, although the GPC molecular weights of the Hf-containing polymers were higher.

Co-reduction of 75% PhCCl$_3$ with 25% CpTiCl$_3$ gives a polymeric material which, by the elemental analysis, has an empirical formula of [(PhC)$_{0.976}$(CpTi)$_{0.024}$]$_n$ (7). The presence of the Cp ligand is confirmed by resonances in the $^1$H and $^{13}$C NMR spectra of 7, at 3.2 and 116 ppm respectively, which are characteristic of this ligand. Integration of the Cp resonance at 3.2 ppm in the $^1$H NMR spectrum of 7 with the phenyl proton resonance at 7.2 ppm gives an empirical formula of [(PhC)$_{0.97}$(CpTi)$_{0.03}$]$_n$, confirming the empirical formula derived from elemental analysis. Polymer 7 shows all the characteristic spectral properties of the polycarbyne networks, including an absence of C=C stretches in its IR spectrum and the characteristic broad electronic absorption band. The polycarbyne network therefore appears to be present, with CpTi units incorporated. In copolymers of silynes with CpTi, sharp resonances in the Si spectrum at −15 to −20 ppm indicate the presence of Ti—Si bonds, suggesting that the CpTi units had been incorporated covertly into the silicon network backbone. No spectral data yet observed for 7 indicates how the CpTi units may be incorporated in the [PhC]$_n$ macromolecules, but structures analogous to the silyne/CpTi polymers are indicated by the very similar NMR and electronic spectra of the materials.

H. Synthesis of Poly(phenylcarbyne-co-pentamethylcyclopentadienylhafnium)

95:5 Poly(phenylcarbyne-co-pentamethylcyclopentadienylhafnium), [(PhC)$_{0.95}$(CP*Hf)$_{0.05}$]$_n$ (8). The synthesis of poly(phenylcarbyne-co-pentamethylcyclopentadienylhafnium) was also performed in accordance with Equation 6.

0.75 PhCCl$_3$ + 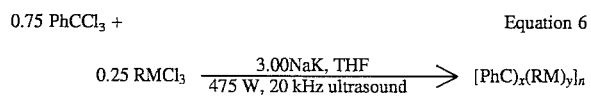 [PhC)$_x$(RM)$_y$]$_n$  Equation 6

R = Cp, M = Ti
R = Cp*, M = Hf

α,α,α-Trichlorotoluene (5.3 mL, 75 mmol) and pentamethylcyclopentadienylhafnium trichloride (5.0 g, 25 mmol, in 25 mL of THF) were reduced with NaK (4.37 mL, 300 mequiv) following the same procedure used to prepare 3. The product was purified by sequential precipitation from THF solution with water, methanol and ethanol. This procedure gave 0.70 g (7%) of [(PhC)$_{0.95}$(Cp*Hf)$_{0.05}$]$_n$ (8) as a tan powder: 1H NMR δ7.2 (br, C$_6$H$_5$), 1.9 (br, CH$_3$); integration gives an empirical formula of [(PhC)$_{0.94}$(Cp*Hf)$_{0.06}$]$_n$; $^{13}$C{$^1$H} NMR δ140, 128 (CC$_6$H$_5$), 120 (C$_5$Me$_5$), 18 (CH$_3$); IR (KBr pellet, cm$^{-1}$) 3445(w), 3023, 2963(m), 1952(m), 1872(m), 1720(m), 1598(s), 1492(vs), 1443(vs), 1066(m), 912(s), 756(s), 697p(vs); GPC (THF versus polystyrene): M$_w$=5009, M$_n$=3965, polydispersity=1.26; electronic spectrum (cyclohexane): onset at 500 nm, increasing gradually with decreasing wavelength to 200 nm. Anal.: Calc. for (PhC)$_{0.9506}$(Cp*Hf)$_{0.0494}$: C, 85.70; H, 5.49; Hf, 8.81; Found: C, 71.49; H, 5.56; Hf, 8.81.

Co-reduction of 75% PhCCl$_3$ with 25% Cp*HfCl$_3$ gives a polymeric material which, by the elemental analysis, has an empirical formula of [(PhC)$_{0.9506}$(Cp*Hf)$_{0.0494}$]$_n$ (8). The presence of the Cp* ligand is confirmed by resonances in the $^1$H and $^{13}$C NMR spectra of 8, at 1.9 and 120 ppm respectively, which are characteristic of this ligand. Integration of the Cp* resonance at 1.9 ppm in the $^1$H NMR spectrum of 8 with the phenyl proton resonance at 7.2 ppm gives an empirical formula of [(PhC)$_{0.94}$(Cp*Hf)$_{0.06}$]$_n$, confirming the empirical formula derived from elemental analysis. Polymer 8 again shows all the characteristic spectral properties of the polycarbyne networks, including an absence of C=C stretches in its IR spectrum and the characteristic broad electronic absorption band. The polycarbyne network therefore appears to be present, with Cp*Hf units now incorporated. The syntheses of 7 and 8 demonstrate that metals, as well as silicon, can be incorporated into polycarbynes. The successful introduction of metals into the polycarbynes suggests that other elements may also be successfully used to tailor the reactivity, pyrolysis properties and products, and electronic behavior of the network carbon polymers.

I. Synthesis of Terpolymers

To synthesize any terpolymer, in which the backbone contains three (or, even more) elements, the appropriate monomers (RMX$_3$ or MX$_4$ for M=C, Si, Ge, Sn, Pb, Ti, Zr, Hf, and X= a halogen or alkoxide; MX$_3$ or MX$_5$ where M= a Group 13 or Group 15 element and X= a halogen, acetate, or alkoxide; $MX_2$ where M= a Group 16 element and X= a hydrogen, alkoxide, or a silyl group; $RNH_2$ for nitrogen; $LnX_2$ or $LnX_3$ where Ln= a lanthanide metal and X= a halogen, acetate, or diketonate ion; other transition metals such as tungsten can also be incorporated by using the appropriate monomer) are added in the desired ratios to the sonicated solution of THF (or any other appropriate organic solvent, such as toluene, alkanes, dimethoxyethane or other ethers, etc.)/NaK alloy following procedures analogous to those used in making the homo- and copolymers discussed above. Usually the major network-forming monomer ($RCCl_3$ or $RSiCl_3$) is partially added first, and others then added with the rest of the major network-forming monomer over the usual 10–20 minute time period. Purification would proceed in the same way as the others. In general, adding any monomer or any number of different monomers to the same general reaction procedure would lead to the incorporation of those monomers into the network.

J. Other Methods for Producing Polycarbyne Polymers

Other starting materials can be used to produce polycarbyne polymers of the present invention. Use of different monomers as starting materials, especially those with more easily-removed leaving groups than chloride, would allow larger yields and incorporation of monomers which are now sluggish to react and difficult to incorporate (for example, MeC). Specific examples would be monomers of the class $RCBr_3$ or $RCI_3$ (J. Villieras et al., *Bull. Soc. Chim. France* 7/8:1797–1802 (1975)).

Other methods can be used to produce the polycarbyne polymers of the present invention. These methods include, but are not limited to, the following: (a) Reduction of the same types of monomers in a solution of metals (such as Na, K, lanthanides, or cesium) in liquid ammonia without ultrasound, in place of the current sonicated NaK/organic solvent system; (b) Reduction of the monomers with a catalytic magnesium/anthracene system instead of with sonication/NaK alloy (H. Bonneman et al., *Agnew. Chem int. Ed. Eng.* 22:728 (1983); B. Bogdanovic et al., *Chem. Ber.* 117:1378 (1984); (c) Reduction of the monomers with any alkali metal at or near its melting point in an appropriate organic solvent, using crown ethers as phase-transfer catalysts (K. Furukawa et al., *Macromolecules* 23:3423 (1990)); (d) Reduction of the monomers with Rieke metals, using anthracene or crown ethers as phase-transfer catalysts (Xiong & Rieke, *J. Org. Chem.* 54:3247 (1989); T. C. Wu et al., *J. Org. Chem.* 55:5045 (1990); R. A. O'Brien et al., *J. Org. Chem.* 57:2667 (1992)).

III. Utility of the Polymers

The primary utility of the polymers of the present invention is as a polymer precursor which can be easily converted to diamond or diamond-like hard carbon materials. Many of the industrial grade diamonds produced today are produced using conventional technology invented and commercialized by General Electric in the 1950s (F. P. Bundy et al., *Nature* 176:51–54 (1955); P. W. Bridgeman, *Sci. Am.* 193:42–46 (1955)). The conventional process involves very high temperatures which can be expensive. The present invention offers a less expensive and easier means of producing industrial grade diamonds or hard carbon materials than conventionally available.

The advantages of using a polymer of the present invention to produce diamond or diamond-like hard carbon materials include the ability to operate from the liquid state. The polymers are soluble and can be converted in situ into films or coatings. Additionally, hard carbon material can be produced at lower temperatures and pressures than with conventional methods. There are several other advantages to producing diamond or diamond-like hard carbon from a polymer precursor. For example, the polymer precursor solution can penetrate a matrix, such as a carbon fiber matrix, to produce a diamond or hard carbon reinforcing filler upon pyrolysis. Additionally, the polymer precursor undergoes a photooxidation reaction so that it may be photopatternable.

Since the polymer precursor of the present invention is soluble in organic solvents, a diamond or diamond-like hard carbon coating can be produced by coating a substrate material with a solution containing the polymer precursor, and then pyrolyzing the coating. Diamond films are conventionally created using chemical vapor deposition (CVD), an expensive process. Many CVD processes use low pressure and temperatures around 800° C. The major problems with CVD are expensive apparatus, sometimes poor adhesion of diamond films to substrates, and slow deposition rates (0.1 to 10 μm/hour). References: K. E. Spear, *J. Am. Ceram. Soc.* 72:171–191 (1989); A. W. Phelps et al., in *Diamond, Boron Nitride, Silicon Carbide, and Related Wide Bandgap Semiconductors*, J. T. Glass et al. Eds. (Materials Research Society, Pittsburgh, Pa., 1989), pp. 213–217; T. Sekine et al., *J. Mater. Sci.* 22:3615 (1987); Yarbrough & Messier, *Science* 247:688 (1993); R. J. Nemanich et al., *J. Vac. Sci. Technol. A* 6:1783 (1988); W. Howard et al., *J. Appl. Phys.* 68:1247 (1990); M. Frenklach et al., *App. Phys. Lett.* 59:546 (1991); Angus & Hayman, *Science* 241:913 (1988); Bachmann & Messier, *Chemical and Engineering News* 67(20):24 (1989); R. Messier, Ed., *New Diamond Science and Technology* (Materials Research Society, Pittsburgh, Pa., 1991); G. H. Johnson et al., Eds., *New Diamond and Diamond-Like Materials Synthesis* (Materials Research Society, Pittsburgh, Pa., 1988); Tsai, & Bogy, *J. Vac. Sci. Technol.* 5:3287 (1987); J. C. Angus et al., *Ann. Rev. Mater. Sci.* 21:221 (1991); S. R. Kasi et al., *Angew. Chem. Int. Ed. Engl.* 27:1203 (1988); M. Frenklach, in *Diamond and Diamond-Like Films and Coatings*, J. C. Angus et al., Eds.; (Plenum, New York, 1991), pp. 499–523.

A. Conversion of the Polymer Precursor

The structure of the poly(phenylcarbyne) three-dimensional atomic network, with its $sp^3$ bonding, and that of crystalline diamond are very similar, especially when contrasted with the structure of polymer networks formed by molecular repeat units. Because of this similarity in structure, the poly(phenylcarbyne) three-dimensional atomic network can be easily converted to the three dimensional diamond crystal structure.

Carbyne-based polymers display unique reactivity owing to the $sp^3$-network backbone structure. Pyrolysis of 1 at atmospheric pressure under inert atmosphere gives predominantly $sp^3$-carbon phases, including diamond or diamond-like carbon, whereas other carbon-based polymers produce principally $sp^2$-hybridized carbon (such as graphite, glassy carbon, or carbon black). For example, poly(diphenylacetylene) (PDPA) is the organic polymer which is chemically identical to poly(phenylcarbyne), but which lacks the $sp^3$-carbon network backbone which is the unique structural feature of 1. Both 1 and PDPA are pyrolytic precursors to carbon, but the pyrolytic conversion of poly(phenylcarbyne) gives predominantly $sp^3$-carbon phases, including diamond or diamond-like carbon, while PDPA produces principally $sp^2$-carbon. The difference in the amount of $sp^3$- and $sp^2$- hybridized carbon in the pyrolysis products given by these stoichiometrically identical polymers, and the formation of diamond or diamond-like carbon by the decomposition of 1, are attributable to the presence in the backbone of 1 of the three-dimensional network of tetrahedral carbon atoms, as opposed to the $sp^2$-hybridized carbons that make up the backbone of polyacetylenes. These results show that, during pyrolysis, conversion of the $sp^3$-bonded carbon network to predominantly $sp^3$-bonded carbon phases is favored even at atmospheric pressure. High-molecular weight carbon network polymers consisting of linear or "hyperbranched" $sp^2$-based molecules are reported to pyrolyze to give glassy (M. R. Callstrom et al., *J. Am. Chem. Soc.* 112:4954 (1990)) or amorphous carbon (Kim & Webster, *J. Am. Chem. Soc.* 112:4592, (1990)), not $sp^3$-phases, again confirming that it is the already-present, all tetrahedral-carbon microstructure of poly(phenylcarbyne) that is the critical feature in allowing its facile conversion to diamond-like carbon, and not simply the presence of a carbon network.

The Raman spectra of the carbon obtained from these pyrolyses give further information about the structures of the materials. No first-order Raman bands are seen in the 2900 to 3100 $cm^{-1}$ or the 2100 to 2300 $cm^{-1}$ regions, strongly suggesting the absence of C—H bonds and C—C triple bonds in this material. The Raman spectrum of the black, reflective regions of the carbon obtained from the pyrolysis of 1 (FIG. 3, bottom) shows peaks corresponding to $sp^2$-carbon (1355 and 1607 $cm^{-1}$) and a broad shoulder centered at 1140 $cm^{-1}$, which is not seen in the carbon obtained from the pyrolysis of PDPA. Many nanocrystalline diamond samples show this feature, which is thought to arise from the effects of small crystallite size or disorder in the tetrahedral carbon network (W. A. Yarbrough, R. Messier, *Science* 247, 688, 1993). This feature has also been attributed to regions of amorphous or microcrystalline diamond, or to a precursor to crystalline diamond (R. J. Nemanich, J. T. Glass, G. Lucovsky, R. E. Shroder, *J. Vac. Sci. Technol.* A 6, 1783, 1988). Its presence here suggests that even the predominantly-$sp^2$ regions of the carbon formed by pyrolysis of 1 may contain some percentage of $sp^3$-hybridization.

Thermal gravimetric analysis shows that the thermal decomposition of 1 begins at 200° C. and is complete at 450° C., having reached a constant weight of 40–45% of the initial. Annealing to 1000° C. or 1600° C. improves the transparency of the carbon product.

The conversion properties and yield of the polymer precursor of the present invention, and the quality of the diamond-like or hard carbon products obtained from them, could be optimized by the use of sidegroups other than phenyl and by more sophisticated processing techniques than simple pyrolysis. For example, other methods of processing polycarbynes include the following: (1) For poly(phenylcarbyne), removal of the phenyl (Ph) rings by reaction with ozone or hydrogen or oxygen plasma, then conversion of the remaining backbone carbons to diamond-like material by pyrolysis; (2) Reaction of the polymers as films under hydrogen or hydrogen plasma at low temperatures (250°–400° C.); (3) Heating polymer films in an inert atmosphere with varying small percentages of $H_2$ and/or $O_2$; (4) All of the above procedures, carried out under pressures of <0.5 GPa; (5) All of the above procedures, at both atmospheric and the pressures given above, with the addition of seed crystals of various types (diamond and/or SiC of micron to nanometer size, or cubane or dodecahedrane species, as nucleation aids; (6) Treatment of polymer films with microwave radiation, in the presence of an inert atmosphere or any of the reactive atmospheres given above; (7) High-power laser irradiation of polymer films or powder, in a patterned array if desired, under either an inert atmosphere or any of the atmospheres listed above; and (8) UV irradiation of the polymer films in the presence of $H_2$ or $H_2$ plasma, followed or accompanied by heating as needed up to approximately 800° C.; and (9) All of the above can be done with temperature variation, from 200° C. to approximately 500° C.

B. Specific Uses for the Polymer Precursor

Diamond or hard carbon materials can be formed by pyrolysis of the poly(phenylcarbyne) class of polymers at pressures and temperatures that are low compared to those used in conventional processes for forming diamond or hard carbon material. This indicates that this class of polymers is a useful precursor to diamond or hard carbon materials.

In addition, the polycarbyne class of polymers are soluble in organic solvents. As a result, these soluble, film-forming polymers can be used to coat substrates with a diamond or hard carbon precursor which can then be pyrolyzed to form an adherent film. Silicon wafers, quartz and Pyrex glass, and some metals (various grades of iron) have been coated with films of poly(phenylcarbyne) by spinning or dip-coating from solutions of the polymers in organic solvents. The films are up to 1–2 μm thick. These polymers films have been converted or processed to form adherent hard carbon films by various methods (simple pyrolysis and treatment with reactive atmospheres described above). The upper limit of the hardness of the diamond or hard carbon material formed by converting polymers in accordance with the present invention has not yet been established. However, it has been observed that the carbon product produced by pyrolysis of poly(phenylcarbyne) easily scratches agate (hardness 6–7 Mohs), and is therefore much harder than graphite (0.5–1 Mohs).

1. Diamond or Hard Carbon Grit

The present invention allows for the production of diamond or hard carbon crystals at lower temperatures and pressures than conventionally used to produce such materials. As a result, diamond and hard carbon can be produced more economically by using the present invention than by using conventional technology. The diamond crystals and hard carbon materials so produced would be suitable for use as abrasives.

2. Adherent Diamond or Hard Carbon Coatings

The polymer precursor of the present invention is soluble in organic solvents. As a result, substrates can be coated with the polymer precursor using any of a number of conventional coating processes, such as spinning or casting. The polymer precursor can then be pyrolyzed to form an adherent diamond or hard carbon coating. As discussed above, silicon wafers, quartz, Pyrex glass, and various grades of iron have been coated with films of poly(phenylcarbyne) which were then processed to form adherent hard carbon films. These adherent hard carbon films cannot be removed by scraping with stainless steel instruments. They don't peel or flake off on their own, but form continuous films. In the case of the silicon substrates, an interface layer of SiC was formed between the substrate and the hard carbon film. This greatly enhances adherence in general, since the hard carbon film is molecularly bonded to the silicon surface by means of this interface. Therefore, the hard carbon films produced from polycarbynes would adhere well to any substrate which forms a carbide (such as many metals). Because of its adherence properties, a diamond or hard carbon coating produced in accordance with the present invention can be used as an adhesion layer between a substrate and another diamond coating.

Hard carbon and diamond coatings are extremely corrosion resistant, and are biocompatible, making them particularly suitable for use on biomedical implants. Even a small amount of corrosion from a biomedical implant can lead to an adverse host reaction, and diamond or hard carbon materials, such as titanium carbide, are ideal for coating such implants. The cost of such coating, especially on larger implants, using conventional technology such as CVD, would be prohibitive. The present invention allows diamond or hard carbon coatings to be economically formed over large areas. A hard carbon coating formed in accordance with the present invention could be used to coat prosthetic devices, such as joints, or even false teeth.

Adherent hard carbon or diamond films are also useful because they are wear resistant and heat resistant. For example, a hard carbon or diamond film produced with the present invention could be used to coat cutting or drilling edges, pipes, graphite crucibles, magnetic disks, frying pans, polymers, clear substances, or any other object that requires wear or corrosion resistance. The coating can also be made smooth and optically transparent, forming an ideal coating for optical surfaces such as eyeglass or camera lenses. The electronic properties of diamond also make it an ideal material for producing a coating for cold cathode devices.

3. Composites

The fact that the polymer precursor of the present invention is soluble allows the precursor to be introduced into a fiber matrix, such as a carbon or graphite fiber matrix. Pyrolysis leads to a diamond or hard carbon reinforcing filler that permeates the matrix. For example, graphite fibers can be soaked in a solution containing the polymer precursor, and then heated to form a hard carbon reinforcing filler.

4. Lithography

Polymer 1 also undergoes the photooxidation reaction (insertion of oxygen into the carbon-carbon a-bonded network upon UV irradiation) which has been found to be characteristic of the network backbone, and which has allowed the use of polysilynes as photoresists for submicron lithography (R. R. Kunz et al., *J. Vac. Sci. Tech.* B 8:1820 (1990)). Exposure of 1 as a solid or solution to UV light centered at 254 nm in an ambient atmosphere results after several hours in the growth of strong C=O and C—O—C stretching bands in the IR at 1720 and 1180 $cm^{-1}$, respectively. No reaction is seen by IR when linear PDPA is irradiated under identical conditions, again indicating the existence of a network rather than a linear backbone structure for 1. This reactivity indicates that the polycarbynes, like their silicon-based congeners, are photopatternable and therefore useful in photolithographic processes. Laser pyrolysis can be used to get the very small feature sizes available with direct writing.

5. Electronics Applications

Diamond is a good wide band gap semiconductor, with the potential to replace silicon as the primary material used for electronics applications. Diamond could be used for either devices on conventional chips, or as a chip substrate. The present invention is not yet refined enough to produce the large single crystal diamonds necessary for most semiconductor electronics applications. However, the lithographic properties discussed above suggest that the present invention is well suited for further development in this area. It may be possible to build upon the present invention and eventually use diamond widely as a wide band gap semiconductor.

Some electronics applications, however, do not require large single crystals. Diamond and hard carbon are very thermally conductive in that they conduct heat well. As such, diamond or hard carbon coatings produced in accordance with the present invention can be used as heat sinks to draw heat away from silicon chips.

6. True Alloys

As discussed above, the three dimensional polymer network of the present invention need not be formed of carbon alone. For example, titanium, geranium, or silicon can be introduced into the network to form a copolymer, or a terpolymer could be formed with all three. An alloy formed by the pyrolysis of a polymer of the present invention containing C, Si, and Ti atoms in the backbone produces a true alloy. The mixing occurs on the molecular level in the formation of the polymer precursor. A coating produced in this manner does not have the uniformity problems of an alloy coating which is made by conventionally combining silicon carbide and titanium carbide. A silicon-titanium-carbide alloy, or other alloy, formed in accordance with the present invention can be used as hard facings for tools. Alternatively, a silicon-germanium-carbide alloy formed in accordance with the present invention can be used in electronics, such as in solid-state circuit components.

While various embodiments of the present invention have been described above, it should be understood that they have been presented by way of example only, and not limitation. For example, R substituents other than those specifically mentioned herein could be used in the polymers of the present invention. Polymers having n of approximately 1200 have been synthesized, but no upper limit on n is known. Elements other than those specifically mentioned herein could be incorporated into the network backbone of the polymers of the present invention. Based upon the teachings herein, the appropriate starting materials and methods of synthesis could be selected to produce the desired polycarbyne polymer. Thus, the breadth and scope of the present invention should not be limited by any of the above described exemplary embodiments, but should be defined only in accordance with the following claims and their equivalents.

What is claimed is:

1. A polymer of the Formula (I):

$$[CR]_n \qquad (I)$$

wherein said polymer comprises tetrahedrally hybridized carbon atoms linked to each other by three carbon-carbon single bonds into a three-dimensional continuous random network backbone, and one R linked to each of said carbon atoms, wherein R is the same or different and selected from the group consisting of H, a saturated linear or branched-chain hydrocarbon containing from 1 to 30 carbon atoms, an unsaturated ring hydrocarbon containing 5 to 14 carbon atoms in the ring, each in unsubstituted or substituted form; wherein the substituent groups are at least one of halogen, nitro, cyano, alkoxy, carboxy, aryl, hydroxy, heterocyclic alkyl, or heterocyclic aryl groups; a halogen, a Group 4 metal, and a Group 13 through Group 16 element, and n is at least 8.

2. The polymer of claim 1, wherein R is —$C_6H_5$.

3. The polymer of claim 1, wherein R is —$CH_3$.

4. The polymer of claim 1, wherein R is the same or different and selected from the group consisting of —$C_6H_5$, —$CH_3$ or H.

5. The polymer of claim 1, wherein R is the same or different and selected from the group consisting of —$CH_6H_5$ or —$CH_3$.

\* \* \* \* \*